(12) United States Patent
Archer et al.

(10) Patent No.: US 6,849,442 B1
(45) Date of Patent: Feb. 1, 2005

(54) BIOSENSOR MATERIALS AND METHODS

(75) Inventors: John Anthony Charles Archer, Cambridge (GB); David Keith Summers, Cambridge (GB); Herve Jacquiau Roland, Cambridge (GB); Justin Antoine Christian Powell, Cambridge (GB)

(73) Assignee: Cambridge University Technical Services Limited, Cambridge (GB)

( * ) Notice: Subject to any disclaimer, the term of this patent is extended or adjusted under 35 U.S.C. 154(b) by 0 days.

(21) Appl. No.: 09/446,681

(22) PCT Filed: Jun. 29, 1998

(86) PCT No.: PCT/GB98/01893

§ 371 (c)(1),
(2), (4) Date: Mar. 14, 2000

(87) PCT Pub. No.: WO99/00517

PCT Pub. Date: Jan. 7, 1999

(30) Foreign Application Priority Data

Jun. 27, 1997 (GB) .............................. 9713666

(51) Int. Cl.$^7$ .......................... C12N 1/21; C12N 15/63; C07H 21/04
(52) U.S. Cl. ................................ 435/252.3; 435/320.1; 435/476; 536/23.1; 536/24.1
(58) Field of Search .......................... 435/252.3, 320.1, 435/476, 325, 455; 536/23.1, 24.1

(56) References Cited

FOREIGN PATENT DOCUMENTS

| EP | 0168933 | | 1/1986 | |
|----|---------|---|--------|---|
| EP | 713 914 | * | 5/1996 | ................. 435/480 |
| EP | 719 862 | * | 7/1996 | ................. 435/480 |
| EP | 0759474 | | 2/1997 | |
| WO | WO9215687 | | 9/1992 | |
| WO | WO9413831 | | 6/1994 | |

OTHER PUBLICATIONS

Li et al. Genetic analysis of the dsz promoter and associated regulatory regions of Rhodococcus erythropolis IGTS8. J. Bacteriol. vol. 178(22):6409–6418, Nov. 1996.*

H. Komeda et al., "Transcriptional Regulation of the Rhodococcus Rhodochrous J1 Nita Gene Encoding a Nitrilase", Proceedings of the National Academy of Sciences of USA, 93: 10572–10577 (1996).

M.Z. Li, "Genetic Analysis of the DSZ Promoter and Associated Regulatory Regions of Rhodococcus Erythropolis IGTSB", J. Bacteriol., 178(22): 6409–6418 (1996).

K. Riedel et al., "Microbial Sensor for Determination of Aromatics and Their Chloroderivatives. Part II: Determination of Chlorinated Phenols Using a Rhodococcus–Containing Biosensor", Appl. Microbiol. Biotechnol., 38: 556–559 (1996).

* cited by examiner

*Primary Examiner*—Terry McKelvey
*Assistant Examiner*—Nancy T. Vogel
(74) *Attorney, Agent, or Firm*—Dann, Dorfman, Herrell & Skillman, P.C.

(57) ABSTRACT

Disclosed are methods for generating mycolic acid bacterial biosensors for particular analytes (especially industrial pollutants) by the use of innovative methods for isolating DNA encoding an inducible promoter which is induced in response to the specific analyte (and/or associated operon proteins), the methods generally comprising the steps of: (a) culturing a source of mycolic acid bacteria in a selective medium containing said specific analyte and being selective for oligotriphic bacteria; (b) identifying mycolic acid bacteria capable of subsisting on said medium, especially those which do not display catabolic repression; (c) extracting DNA from said mycolic acid bacteria; (d) incorporating said DNA into vectors, such as various shuttle vectors; (e) cloning said vector into a suitable host cell (which may be *E. coli* strain carrying one or more of the mcrABC mrr hsdSRM recA and recO mutations); (f) screening that host cell (or a second host cell which is preferably a *corynebacterium*) for said inducible promoter. The methods are exemplified by the isolation of the *R. corallina* ohp operon.

16 Claims, 17 Drawing Sheets

Figure 1:
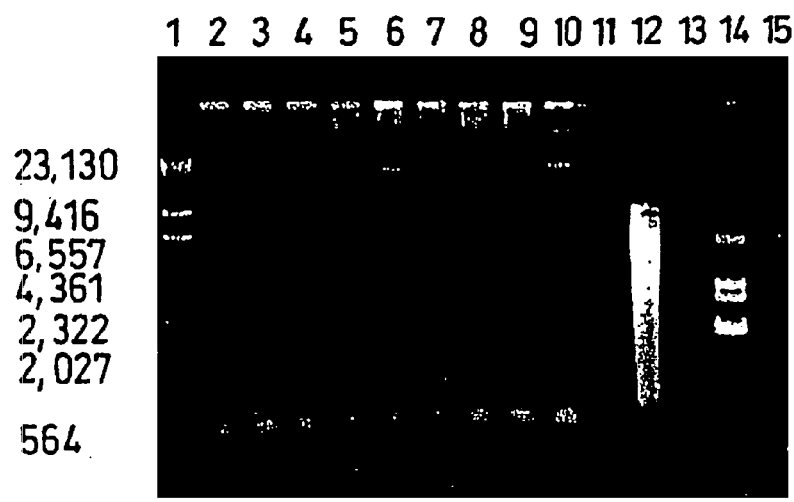

| Gene | Initiator Codon | Terminator Codon | Molecular Weight |
|---|---|---|---|
| Regulator | 295 | 1035 | 27102 |
| Transport | 1450 | 2805 | 47433 |
| Monooxygenase | 2810 | 4720 | 69650 |
| Hydroxymuconic semialdehyde hydrolase | 4717 | 5586 | 32770 |
| Catechol 2, 3-dioxygenase | 5721 | 6665 | 33894 |
| Alcohol dehydrogenase | 6711 | 7580 | 30586 |

Fig. 4A

```
                  10                        30                        50
                   .                         .                         .
     GAATTCCATGTTCTTCTCCTTGCATGTGGCCCGCGTTGCCGAGGGCACTGCTCGGCCTGT
     CTTAAGGTACAAGAAGAGGAACGTACACCGGGCGCAACGGCTCCCGTGACGAGCCGGACA 70                        90                       110
                   .                         .                         .
     CGCCCGCAGAGGGCGCATGTCCGGGTGCCTGGATATGGCGCGTACGGCGTGCCCTCCGGC
     GCGGGCGTCTCCCGCGTACAGGCCCACGGACCTATACCGCGCATGCCGCACGGGAGGCCG 130                       150                       170
                   .                         .                         .
     GTTAACCCCGAGGTTGGCCACGATGCCCCGGCCATCAGGTCTGGAATGCTAGCGTTCCAG
     CAATTGGGGCTCCAACCGGTGCTACGGGGCCGGTAGTCCAGACCTTACGATCGCAAGGTC 190                       210                       230
                   .                         .                         .
     ACGAAGGTAACCCACAGTGACTCACACCACAAGTACTAGAATGCAAGCTGTTGCGGTGAG
     TGCTTCCATTGGGTGTCACTGAGTGTGGTGTTCATGATCTTACGTTCGACAACGCCACTC 250                       270                       290
                   .                         .                         .
     CGCCGCGGCATAAGGGGGAGCCATGTCCGGGACGCCGACGGAAAGCCTGACTCGATGACC
     GCGGCGCCGTATTCCCCCTCGGTACAGGCCCTGCGGCTGCCTTTCGGACTGAGCTACTGG
                                                             M   T 310                       330                       350
                   .                         .                         .
     ACCACCGACACCGGCCCCAAGCCGGGCAGTGAGGCCGCCGCCCTGCTCGCCAATGTCCGC
     TGGTGGCTGTGGCCGGGGTTCGGCCCGTCACTCCGGCGGCGGGACGAGCGGTTACAGGCG
     T   T   D   T   G   P   K   P   G   S   E   A   A   A   L   L   A   N   V   R 370                       390                       410
                   .                         .                         .
     ACCTCGGGGGCGCGGCTGTCCTCCGCGTTGTACGACATTCTGAAGAACCGGCTGCTCGAA
     TGGAGCCCCCGCGCCGACAGGAGGCGCAACATGCTGTAAGACTTCTTGGCCGACGAGCTT
     T   S   G   A   R   L   S   S   A   L   Y   D   I   L   K   N   R   L   L   E 430                       450                       470
                   .                         .                         .
     GGGCGCTATGCGGCAGGCGAGAAGATCGTCGTCGAGTCGATCCGGCAAGAGTTCGGGGTG
     CCCGCGATACGCCGTCCGCTCTTCTAGCAGCAGCTCAGCTAGGCCGTTCTCAAGCCCCAC
     G   R   Y   A   A   G   E   K   I   V   V   E   S   I   R   Q   E   F   G   V 490                       510                       530
                   .                         .                         .
     AGCAAGCAGCCCGTCATGGACGCTCTGCGCCGCCTGTCCAGCGACAAGCTGGTCCACATC
     TCGTTCGTCGGGCAGTACCTGCGAGACGCGGCGGACAGGTCGCTGTTCGACCAGGTGTAG
     S   K   Q   P   V   M   D   A   L   R   R   L   S   S   D   K   L   V   H   I 550                       570                       590
                   .                         .                         .
     GTTCCCCAGGTCGGTTGCGAGGTCGTCTCCTACGCCCCGCGCGAAGTGGAAGACTTCTAC
     CAAGGGGTCCAGCCAACGCTCCAGCAGAGGATGCGGGCGCGCTTCACCTTCTGAAGATG
     V   P   Q   V   G   C   E   V   V   S   Y   A   P   R   E   V   E   D   F   Y 610                       630                       650
                   .                         .                         .
     ACCCTGTTCGGCGGTTTCGAAGGGACCATCGCCGCGGTAGCGGCCTCCCGGCGGACCGAG
```

Fig. 4B

```
      TGGGACAAGCCGCCAAAGCTTCCCTGGTAGCGGCGCCATCGCCGGAGGGCCGCCTGGCTC
       T  L  F  G  G  F  E  G  T  I  A  A  V  A  A  S  R  R  T  E
             670                 690                 710
      GCCCAGTTGCTGGAGCTGGACCTGATCTCGGCGCGGGTCGACGCCCTGATCACCTCCCAC
      CGGGTCAACGACCTCGACCTGGACTAGAGCCGCGCCCAGCTGCGGGACTAGTGGAGGGTG
       A  Q  L  L  E  L  D  L  I  S  A  R  V  D  A  L  I  T  S  H
             730                 750                 770
      GACCCGGTGGTCCGCGCCCGCGGGTACCGCGTGCACAACCGGGAGTTCCATGCGGCCATC
      CTGGGCCACCAGGCGCGGGCGCCCATGGCGCACGTGTTGGCCCTCAAGGTACGCCGGTAG
       D  P  V  V  R  A  R  G  Y  R  V  H  N  R  E  F  H  A  A  I
             790                 810                 830
      CACGCGATGGCGCACTCGCGGATCATGGAGGAGACCAGCCAGCGAATGTGGGATCTGTCG
      GTGCGCTACCGCGTGAGCGCCTAGTACCTCCTCTGGTCGGTCGCTTACACCCTAGACAGC
       H  A  M  A  H  S  R  I  M  E  E  T  S  Q  R  M  W  D  L  S
             850                 870                 890
      GACTTCTTGATCAACACCACCGGCATCACCAACCCGCTCTCGAGCGCACTGCCCGACCGG
      CTGAAGAACTAGTTGTGGTGGCCGTAGTGGTTGGGCGAGAGCTCGCGTGACGGGCTGGCC
       D  F  L  I  N  T  T  G  I  T  N  P  L  S  S  A  L  P  D  R
             910                 930                 950
      CAGCATGACCACCACGAAATCACCGAGGCCATCCGCAACCGTGACGCAGCTGCCGCCCGC
      GTCGTACTGGTGGTGCTTTAGTGGCTCCGGTAGGCGTTGGCACTGCGTCGACGGCGGGCG
       Q  H  D  H  H  E  I  T  E  A  I  R  N  R  D  A  A  A  A  R
             970                 990                 1010
      GAGGCCATGGAACGCCACATCGTCGGCACCATCGCAGTAATCCGCGACGAATCCAACGCC
      CTCCGGTACCTTGCGGTGTAGCAGCCGTGGTAGCGTCATTAGGCGCTGCTTAGGTTGCGG
       E  A  M  E  R  H  I  V  G  T  I  A  V  I  R  D  E  S  N  A
             1030                1050                1070
      CAGCTGCCGAGCTAGACCCCGATACCCGGGCCATCGACCGGCTCCGCTATCGCGCCACCT
      GTCGACGGCTCGATCTGGGGCTATGGGCCCGGTAGCTGGCCGAGGCGATAGCGCGGTGGA
       Q  L  P  S  *
             1090                1110                1130
      ACGCCGAGGGGGGACTCTCGGCCGTAGCGCTGCAGACGATCCACCGGCACCCTCCACGCT
      TGCGGCTCCCCCCTGAGAGCCGGCATCGCGACGTCTGCTAGGTGGCCGTGGGAGGTGCGA
             1150                1170                1190
      GACCCCTGTCTCGCCCTAGAGGGCCGGCGCGCCGTCGATCACCTTTACCCTCATCCAGAG
      CTGGGGACAGAGCGGGATCTCCCGGCCGCGCGGCAGCTAGTGGAAATGGGAGTAGGTCTC
             1210                1230                1250
      ACTTGCGTCACCCTCTATGCCCGAGTAGCGTCTGAACTAGACGTCTAGCATTCTAGTTGA
      TGAACGCAGTGGGAGATACGGGCTCATCGCAGACTTGATCTGCAGATCGTAAGATCAACT
             1270                1290                1310
      GTGCTCCCTCTCGAAGATTCTCCAGAGAACCCCTCTCGAACATCCCCAGAAGAAAGGAGC
```

Fig. 4C

```
CACGAGGGAGAGCTTCTAAGAGGTCTCTTGGGGAGAGCTTGTAGGGTCTTCTTTCCTCG
         1330             1350             1370
GGCCATGACGACCGCTTCGCACGCATCGTCCTTCGGGGCACGAGCCCACTTCCGCCCACA
CCGGTACTGCTGGCGAAGCGTGCGTAGCAGGAAGCCCCGTGCTCGGGTGAAGGCGGGTGT
         1390             1410             1430
GATCGGGGAAGCCCGACCGTGAGCACCACACCTACCTCCCCGACGAAGACCTCACCGCTG
CTAGCCCCTTCGGGCTGGCACTCGTGGTGTGGATGGAGGGGCTGCTTCTGGAGTGGCGAC
         1450             1470             1490
CGGGTAGCGATGGCCAGCTTCATCGGTACCACCGTCGAGTACTACGACTTCTTCATCTAC
GCCCATCGCTACCGGTCGAAGTAGCCATGGTGGCAGCTCATGATGCTGAAGAAGTAGATG
         M  A  S  F  I  G  T  T  V  E  Y  Y  D  F  F  I  Y
         1510             1530             1550
GGCACCGCGGCCGCGCTGGTATTCCCTGAGTTGTTCTTCCCGGATGTCTCGTCCGCGATC
CCGTGGCGCCGGCGCGACCATAAGGGACTCAACAAGAAGGGCCTACAGAGCAGGCGCTAG
G  T  A  A  A  L  V  F  P  E  L  F  F  P  D  V  S  S  A  I
         1570             1590             1610
GGAATCCTGTTGTCGTTCGCGACCTTCAGCGTTGGGTTCCTCGCCCGCCCGCTGGGTGGC
CCTTAGGACAACAGCAAGCGCTGGAAGTCGCAACCCAAGGAGCGGGCGGGCGACCCACCG
G  I  L  L  S  F  A  T  F  S  V  G  F  L  A  R  P  L  G  G
         1630             1650             1670
ATAGTGTTCGGGCACTTCGGTGACCGGGTCGGCCGCAAGCAGATGCTGGTGATCTCCCTG
TATCACAAGCCCGTGAAGCCACTGGCCCAGCCGGCGTTCGTCTACGACCACTAGAGGGAC
I  V  F  G  H  F  G  D  R  V  G  R  K  Q  M  L  V  I  S  L
         1690             1710             1730
GTCGGAATGGGCTCGGCCACCGTACTGATGGGATTGTTGCCCGGTTACGCCCAAATCGGG
CAGCCTTACCCGAGCCGGTGGCATGACTACCCTAACAACGGGCCAATGCGGGTTTAGCCC
V  G  M  G  S  A  T  V  L  M  G  L  L  P  G  Y  A  Q  I  G
         1750             1770             1790
ATCGCCGCCCCCATCCTGCTGACCCTGCTGCGCCTGGTGCAGGGCTTTGCCGTCGGCGGC
TAGCGGCGGGGGTAGGACGACTGGGACGACGCGGACCACGTCCCGAAACGGCAGCCGCCG
I  A  A  P  I  L  L  T  L  L  R  L  V  Q  G  F  A  V  G  G
         1810             1830             1850
GAGTGGGGTGGAGCCACCCTGATGGCCGTCGAGCACGCCCCCACCGCGAAGAAGGGCTTT
CTCACCCCACCTCGGTGGGACTACCGGCAGCTCGTGCGGGGGTGGCGCTTCTTCCCGAAA
E  W  G  G  A  T  L  M  A  V  E  H  A  P  T  A  K  K  G  F
         1870             1890             1910
TTCGGATCCTTCTCCCAGATGGGGGCACCCGCCGGGACCAGCGTCGCAACCCTGGCGTTC
AAGCCTAGGAAGAGGGTCTACCCCCGTGGGCGGCCCTGGTCGCAGCGTTGGGACCGCAAG
F  G  S  F  S  Q  M  G  A  P  A  G  T  S  V  A  T  L  A  F
         1930             1950             1970
TTCGCGGTCTCCCAATTGCCCGACGAGCAGTTCCTGAGTTGGGGCTGGCGACTGCCGTTC
```

Fig. 4D

```
AAGCGCCAGAGGGTTAACGGGCTGCTCGTCAAGGACTCAACCCCGACCGCTGACGGCAAG
 F  A  V  S  Q  L  P  D  E  Q  P  L  S  W  G  W  R  L  P  F
        1990                2010                2030
         .                   .                   .
CTGTTCAGCGCGGTGCTGATCGTGATCGGGCTGTTCATTCGCCTGTCCCTGGCCGAAAGC
GACAAGTCGCGCCACGACTAGCACTAGCCCGACAAGTAAGCGGACAGGGACCGGCTTTCG
 L  F  S  A  V  L  I  V  I  G  L  F  I  R  L  S  L  A  E  S
        2050                2070                2090
         .                   .                   .
CCCGACTTCGCCGAGGTGAAGGCACAGAGCGCCGTGGTGCGAATGCCGATCGCCGAAGCG
GGGCTGAAGCGGCTCCACTTCCGTGTCTCGCGGCACCACGCTTACGGCTAGCGGCTTCGC
 P  D  F  A  E  V  K  A  Q  S  A  V  V  R  M  P  I  A  E  A
        2110                2130                2150
         .                   .                   .
TTCCGCAAGCACTGGAAGGAAATTCTCCTCATCGCGGGCACCTACCTGTCCCAAGGAGTG
AAGGCGTTCGTGACCTTCCTTTAAGAGGAGTAGCGCCCGTGGATGGACAGGGTTCCTCAC
 F  R  K  H  W  K  E  I  L  L  I  A  G  T  Y  L  S  Q  G  V
        2170                2190                2210
         .                   .                   .
TTCGCCTATATCTGCATGGCCTACCTCGTCTCCTACGGCACCACCGTCGCGGGGATCAGC
AAGCGGATATAGACGTACCGGATGGAGCAGAGGATGCCGTGGTGGCAGCGCCCCTAGTCG
 F  A  Y  I  C  M  A  Y  L  V  S  Y  G  T  T  V  A  G  I  S
        2230                2250                2270
         .                   .                   .
CGCACCTTCGCCCTGGCCGGAGTATTCGTCGCCGGCATCGTCGCCGTCCTCCTCTACCTC
GCGTGGAAGCGGGACCGGCCTCATAAGCAGCGGCCGTAGCAGCGGCAGGAGGAGATGGAG
 R  T  F  A  L  A  G  V  F  V  A  G  I  V  A  V  L  L  Y  L
        2290                2310                2330
         .                   .                   .
GTGTTCGGCGCTCTGTCCGACACTTTCGGCCGCAAGACCATGTACCTGCTCGGCGCCGCC
CACAAGCCGCGAGACAGGCTGTGAAAGCCGGCGTTCTGGTACATGGACGAGCCGCGGCGG
 V  F  G  A  L  S  D  T  F  G  R  K  T  M  Y  L  L  G  A  A
        2350                2370                2390
         .                   .                   .
GCGATGGGTGTGGTGATCGCCCCCGCCTTCGCACTGATCAACACCGGCAACCCGTGGCTG
CGCTACCCACACCACTAGCGGGGGCGGAAGCGTGACTAGTTGTGGCCGTTGGGCACCGAC
 A  M  G  V  V  I  A  P  A  F  A  L  I  N  T  G  N  P  W  L
        2410                2430                2450
         .                   .                   .
TTCATGGCCGCGCAGGTGCTGGTCTTCGGAATTGCAATGGCCCCCGCCGCCGGCGTGACA
AAGTACCGGCGCGTCCACGACCAGAAGCCTTAACGTTACCGGGGGCGGCGGCCGCACTGT
 F  M  A  A  Q  V  L  V  F  G  I  A  M  A  P  A  A  G  V  T
        2470                2490                2510
         .                   .                   .
GGCTCCCTGTTCACGATGGTCTTCGACGCGGACGTGCGCTACAGCGGTGTCTCTATCGGC
CCGAGGGACAAGTGCTACCAGAAGCTGCGCCTGCACGCGATGTCGCCACAGAGATAGCCG
 G  S  L  F  T  M  V  F  D  A  D  V  R  Y  S  G  V  S  I  G
        2530                2550                2570
         .                   .                   .
TACACCATCTCCCAGGTCGCCGGCTCCGCGTTCGCCCCGACGATCGCGACCGCCTTGTAC
ATGTGGTAGAGGGTCCAGCGGCCGAGGCGCAAGCGGGGCTGCTAGCGCTGGCGGAACATG
 Y  T  I  S  Q  V  A  G  S  A  F  A  P  T  I  A  T  A  L  Y
```

Fig. 4E 2590          2610          2630
GCCTCCACCAACACCAGCAACTCGATCGTGACCTACCTGCTGATCGTCTCGGCCATCTCG
CGGAGGTGGTTGTGGTCGTTGAGCTAGCACTGGATGGACGACTAGCAGAGCCGGTAGAGC
 A  S  T  N  T  S  N  S  I  V  T  Y  L  L  I  V  S  A  I  S 2650          2670          2690
ATCGTCTCGGTGATCCTGCTGCCCGGCGGCTGGGGGCGCAAGGGCGCTGCGAGCCAGCTC
TAGCAGAGCCACTAGGACGACGGGCCGCCGACCCCCGCGTTCCCGCGACGCTCGGTCGAG
 I  V  S  V  I  L  L  P  G  G  W  G  R  K  G  A  A  S  Q  L 2710          2730          2750
ACTCGCGACCAGGCCACCTCCACACCGAAAATGCCTGACACCGAAACATTTTCGACTCGG
TGAGCGCTGGTCCGGTGGAGGTGTGGCTTTTACGGACTGTGGCTTTGTAAAAGCTGAGCC
 T  R  D  Q  A  T  S  T  P  K  M  P  D  T  E  T  F  S  T  R 2770          2790          2810
ACAGTTCCGGACACCGCAGCATCCCTGCGCGTCCTCGACAAGTGAAGTGATGACAGACAT
TGTCAAGGCCTGTGGCGTCGTAGGGACGCGCAGGAGCTGTTCACTTCACTACTGTCTGTA
 T  V  P  D  T  A  A  S  L  R  V  L  D  K  *        M  T  D  M 2830          2850          2870
GAGTGACCACGACCGCACCTCCTACGACACCGACGTCGTGATCGTCGGCCTCGGCCCCGC
CTCACTGGTGCTGGCGTGGAGGATGCTGTGGCTGCAGCACTAGCAGCCGGAGCCGGGGCG
 S  D  H  D  R  T  S  Y  D  T  D  V  V  I  V  G  L  G  P  A 2890          2910          2930
CGGTGGCACAGCGGCGCTTGCCCTGGCCAGCTACGGCATCCGCGTTCACGCCGTCTCGAT
GCCACCGTGTCGCCGCGAACGGGACCGGTCGATGCCGTAGGCGCAAGTGCGGCAGAGCTA
 G  G  T  A  A  L  A  L  A  S  Y  G  I  R  V  H  A  V  S  M 2950          2970          2990
GTTCCCCTGGGTGGCGAACTCGCCGCGCGCGCACATCACCAACCAGCGCGCCGTCGAAGT
CAAGGGGACCCACCGCTTGAGCGGCGCGCGCGTGTAGTGGTTGGTCGCGCGGCAGCTTCA
 F  P  W  V  A  N  S  P  R  A  H  I  T  N  Q  R  A  V  E  V 3010          3030          3050
GCTGCGTGACCTGGGCGTCGAAGACGAGGCGCGCAACTACGCCACCCCGTGGGACCAGAT
CGACGCACTGGACCCGCAGCTTCTGCTCCGCGCGTTGATGCGGTGGGGCACCCTGGTCTA
 L  R  D  L  G  V  E  D  E  A  R  N  Y  A  T  P  W  D  Q  M 3070          3090          3110
GGGCGACACGCTGTTCACCACGAGCCTGGCCGGCGAGGAGATCGTCCGGATGCAGACCTG
CCCGCTGTGCGACAAGTGGTGCTCGGACCGGCCGCTCCTCTAGCAGGCCTACGTCTGGAC
 G  D  T  L  F  T  T  S  L  A  G  E  E  I  V  R  M  Q  T  W 3130          3150          3170
GGGTACGGGCGATATCCGCTACGGGGACTACCTGTCCGGAAGCCCCTGCACGATGCTCGA
CCCATGCCCGCTATAGGCGATGCCCCTGATGGACAGGCCTTCGGGGACGTGCTACGAGCT
 G  T  G  D  I  R  Y  G  D  Y  L  S  G  S  P  C  T  M  L  D 3190          3210          3230
CATTCCGCAGCCCCTGATGGAGCCGGTGCTGATCAAGAACGCCGCCGAACGTGGTGCGGT

```
           GTAAGGCGTCGGGGACTACCTCGGCCACGACTAGTTCTTGCGGCGGCTTGCACCACGCCA
            I  P  Q  P  L  M  E  P  V  L  I  K  N  A  A  E  R  G  A  V
                 3250               3270               3290

CATCAGCTTCAACACCGAATACCTCGACCACGCCCAGGACGAGGACGGGGTGACCGTCCG
           GTAGTCGAAGTTGTGGCTTATGGAGCTGGTGCGGGTCCTGCTCCTGCCCCACTGGCAGGC
            I  S  P  N  T  E  Y  L  D  H  A  Q  D  E  D  G  V  T  V  R
                 3310               3330               3350

GTTCCGCGACGTCCGCTCGGGCACCGTGTTCACCCAGCGAGCCCGCTTCCTGCTCGGTTT
           CAAGGCGCTGCAGGCGAGCCCGTGGCACAAGTGGGTCGCTCGGGCGAAGGACGAGCCAAA
            F  R  D  V  R  S  G  T  V  F  T  Q  R  A  R  F  L  L  G  F
                 3370               3390               3410

CGACGGCGCACGATCGAAGATCGCCGAACAGATCGGGCTTCCGTTCGAAGGTGAACTCGC
           GCTGCCGCGTGCTAGCTTCTAGCGGCTTGTCTAGCCCGAAGGCAAGCTTCCACTTGAGCG
            D  G  A  R  S  K  I  A  E  Q  I  G  L  P  F  E  G  E  L  A
                 3430               3450               3470

CCGCGCCGGTACCGCGTACATCCTGTTCAACGCGGACCTGAGCAAATATGTCGCTCATCG
           GGCGCGGCCATGGCGCATGTAGGACAAGTTGCGCCTGGACTCGTTTATACAGCGAGTAGC
            R  A  G  T  A  Y  I  L  F  N  A  D  L  S  K  Y  V  A  H  R
                 3490               3510               3530

GCCGAGCATCTTGCACTGGATCGTCAACTCGAAGGCCGGTTTCGGTGAGATCGGCATGGG
           CGGCTCGTAGAACGTGACCTAGCAGTTGAGCTTCCGGCCAAAGCCACTCTAGCCGTACCC
            P  S  I  L  H  W  I  V  N  S  K  A  G  F  G  E  I  G  M  G
                 3550               3570               3590

TCTGCTGCGCGCGATCCGACCGTGGGACCAGTGGATCGCCGGCTGGGGCTTCGACATGGC
           AGACGACGCGCGCTAGGCTGGCACCCTGGTCACCTAGCGGCCGACCCCGAAGCTGTACCG
            L  L  R  A  I  R  P  W  D  Q  W  I  A  G  W  G  F  D  M  A
                 3610               3630               3650

GAACGGCGAGCCGGATGTCTCCGACGACGTTGTCCTCGAACAGATCCGGACCCTCGTCGG
           CTTGCCGCTCGGCCTACAGAGGCTGCTGCAACAGGAGCTTGTCTAGGCCTGGGAGCAGCC
            N  G  E  P  D  V  S  D  D  V  V  L  E  Q  I  R  T  L  V  G
                 3670               3690               3710

CGACCCGCACCTGGACGTCGAGATCGTGTCGAGGTCCTTCTGGTACGTCAACCGGCAGTG
           GCTGGGCGTGGACCTGCAGCTCTAGCACAGCTCCAGGAAGACCATGCAGTTGGCCGTCAC
            D  P  H  L  D  V  E  I  V  S  R  S  F  W  Y  V  N  R  Q  W
                 3730               3750               3770

GGCTGAGCACTACCAGTCCGGTCGAGTGTTCTGCGGCGGCGACGCGGTGCACCGGCATCC
           CCGACTCGTGATGGTCAGGCCAGCTCACAAGACGCCGCCGCTGCGCCACGTGGCCGTAGG
            A  E  H  Y  Q  S  G  R  V  F  C  G  G  D  A  V  H  R  H  P
                 3790               3810               3830

GCCGAGCAGCGGGCTGGGCTCGAACACGTCCATGCAGGACGCGTTCAACCTGGCATGGAA
           CGGCTCGTCGCCCGACCCGAGCTTGTGCAGGTACGTCCTGCGCAAGTTGGACCGTACCTT
            P  S  S  G  L  G  S  N  T  S  M  Q  D  A  F  N  L  A  W  K
```

Fig. 4G

```
           3850                  3870                  3890
              .                    .                     .
GATCGCGTTCGTCGTGAAGGGGTATGCAGGACCGGGTCTGCTCGAGTCCTACTCTCCTGA
CTAGCGCAAGCAGCACTTCCCCATACGTCCTGGCCCAGACGAGCTCAGGATGAGAGGACT
  I  A  F  V  V  K  G  Y  A  G  P  G  L  L  E  S  Y  S  P  E 3910                  3930                  3950
              .                    .                     .
GCGTGTTCCGGTCGGCAAACAGATCGTCGCTCGCGCCAACCAGTCCCGCAAGGACTACGC
CGCACAAGGCCAGCCGTTTGTCTAGCAGCGAGCGCGGTTGGTCAGGGCGTTCCTGATGCG
  R  V  P  V  G  K  Q  I  V  A  R  A  N  Q  S  R  K  D  Y  A 3970                  3990                  4010
              .                    .                     .
CGGGCTGCGCGAATGGTTCGATCACGAGAGCGACGACCCGGTCGCCGCCGGCCTGGCAAA
GCCCGACGCGCTTACCAAGCTAGTGCTCTCGCTGCTGGGCCAGCGGCGGCCGGACCGTTT
  G  L  R  E  W  F  D  H  E  S  D  D  P  V  A  A  G  L  A  K 4030                  4050                  4070
              .                    .                     .
GTTGAAGGAACCCTCGTCCGAAGGTGTTGCTCTGCGTGAGCGGCTGTACGAGGCGCTGGA
CAACTTCCTTGGGAGCAGGCTTCCACAACGAGACGCACTCGCCGACATGCTCCGCGACCT
  L  K  E  P  S  S  E  G  V  A  L  R  E  R  L  Y  E  A  L  E 4090                  4110                  4130
              .                    .                     .
GGTGAAGAACGCCGAATTCAACGCCCAGGGCGTCGAACTCAACCAGCGCTACACCTCGTC
CCACTTCTTGCGGCTTAAGTTGCGGGTCCCGCAGCTTGAGTTGGTCGCGATGTGGAGCAG
  V  K  N  A  E  F  N  A  Q  G  V  E  L  N  Q  R  Y  T  S  S 4150                  4170                  4190
              .                    .                     .
CGCGGTCGTTCCCGACCCCGAGGCGGGCGAGGAAGTGTGGGTGCGCGATCGTGAGCTGTA
GCGCCAGCAAGGGCTGGGGCTCCGCCCGCTCCTTCACACCCACGCGCTAGCACTCGACAT
  A  V  V  P  D  P  E  A  G  E  E  V  W  V  R  D  R  E  L  Y 4210                  4230                  4250
              .                    .                     .
CCTGCAGGCCACCACCCGGCCGGGCGCGAAGCTGCCGCATGCGTGGCTGGTCGGCGCCGA
GGACGTCCGGTGGTGGGCCGGCCCGCGCTTCGACGGCGTACGCACCGACCAGCCGCGGCT
  L  Q  A  T  T  R  P  G  A  K  L  P  H  A  W  L  V  G  A  D 4270                  4290                  4310
              .                    .                     .
CGGAACCCGCATCTCCACCCTCGACGTCACCGGCAAGGGAATGATGACCCTGCTGACCGG
GCCTTGGGCGTAGAGGTGGGAGCTGCAGTGGCCGTTCCCTTACTACTGGGACGACTGGCC
  G  T  R  I  S  T  L  D  V  T  G  K  G  M  M  T  L  L  T  G 4330                  4350                  4370
              .                    .                     .
ACTCGGCGGCCAGGCATGGAAGCGTGCCGCCGCCAAACTCGACCTGCCGTTCCTGCGGAC
TGAGCCGCCGGTCCGTACCTTCGCACGGCGGCGGTTTGAGCTGGACGGCAAGGACGCCTG
  L  G  G  Q  A  W  K  R  A  A  A  K  L  D  L  P  F  L  R  T 4390                  4410                  4430
              .                    .                     .
CGTCGTTGTCGGCGAACCCGGCACCATCGACCCTTACGGATACTGGCGGCGGGTCCGCGA
GCAGCAACAGCCGCTTGGGCCGTGGTAGCTGGGAATGCCTATGACCGCCGCCCAGGCGCT
  V  V  V  G  E  P  G  T  I  D  P  Y  G  Y  W  R  R  V  R  D 4450                  4470                  4490
              .                    .                     .
CATCGACGAGGCCGGCGCCCTGCTCGTGCGGCCCGACGGCTACGTCGCGTGGCGACACAG
```

Fig. 4H

```
GTAGCTGCTCCGGCCGCGGGACGAGCACGCCGGGCTGCCGATGCAGCGCACCGCTGTGTC
 I   D   E   A   G   A   L   L   V   R   P   D   G   Y   V   A   W   R   H   S
        4510              4530              4550

TGCTCCGGTCTGGGACGACACCGAAGCGCTCACCAGCCTCGAGAACGCTCTCACCGCGGT
ACGAGGCCAGACCCTGCTGTGGCTTCGCGAGTGGTCGGAGCTCTTGCGAGAGTGGCGCCA
 A   P   V   W   D   D   T   E   A   L   T   S   L   E   N   A   L   T   A   V
        4570              4590              4610

CCTCGACCACTCGGCCAGCGACAACGGGAACCCGAGCGGCACAAACGAGCCGCAGTACAG
GGAGCTGGTGAGCCGGTCGCTGTTGCCCTTGGGCTCGCCGTGTTTGCTCGGCGTCATGTC
 L   D   H   S   A   S   D   N   G   N   P   S   G   T   N   E   P   Q   Y   S
        4630              4650              4670

CACCCGGGCCGTGCCGATCGTCGTTCCGCACGTTACCGCCGAGGATGCAGCACCAGCTTC
GTGGGCCCGGCACGGCTAGCAGCAAGGCGTGCAATGGCGGCTCCTACGTCGTGGTCGAAG
 T   R   A   V   P   I   V   V   P   H   V   T   A   E   D   A   A   P   A   S
        4690              4710              4730

CGCCACCCGCACCACCACAGTCGAGGGAGAGAACCGATGACCCGTCCTTACACCAGCGTC
GCGGTGGGCGTGGTGGTGTCAGCTCCCTCTCTTGGCTACTGGGCAGGAATGTGGTCGCAG
 A   T   R   T   T   T   V   E   G   E   N   R   *
                                              M   T   R   P   Y   T   S   V
        4750              4770              4790

TGGGACGACCTGAACCAGGTCGAGTTCAGCCAGGGATTCATCCAGGCCGGCCCCTACCGG
ACCCTGCTGGACTTGGTCCAGCTCAAGTCGGTCCCTAAGTAGGTCCGGCCGGGGATGGCC
 W   D   D   L   N   Q   V   E   F   S   Q   G   F   I   Q   A   G   P   Y   R
        4810              4830              4850

ACCCGATACCTGCACGCCGGCGATTCGTCCAAGCCCACGCTGATCCTGCTGCACGGCATC
TGGGCTATGGACGTGCGGCCGCTAAGCAGGTTCGGGTGCGACTAGGACGACGTGCCGTAG
 T   R   Y   L   H   A   G   D   S   S   K   P   T   L   I   L   L   H   G   I
        4870              4890              4910

ACCGGCCACGCCGAGGCGTACGTGCGCAATCTGCGCTCGCATTCCGAGCACTTCAACGTC
TGGCCGGTGCGGCTCCGCATGCACGCGTTAGACGCGAGCGTAAGGCTCGTGAAGTTGCAG
 T   G   H   A   E   A   Y   V   R   N   L   R   S   H   S   E   H   F   N   V
        4930              4950              4970

TGGGCAATCGACTTCATCGGCCACGGCTATTCGACCAAGCCCGACCACCCGCTCGAGATC
ACCCGTTAGCTGAAGTAGCCGGTGCCGATAAGCTGGTTCGGGCTGGTGGGCGAGCTCTAG
 W   A   I   D   F   I   G   H   G   Y   S   T   K   P   D   H   P   L   E   I
        4990              5010              5030

AAGCACTACATCGACCACGTGCTGCAGTTGCTGGACGCCATCGGCGTCGAGAAGGCCTCG
TTCGTGATGTAGCTGGTGCACGACGTCAACGACCTGCGGTAGCCGCAGCTCTTCCGGAGC
 K   H   Y   I   D   H   V   L   Q   L   L   D   A   I   G   V   E   K   A   S
        5050              5070              5090

TTTTCCGGGGAGTCTCTCGGCGGTTGGGTCACCGCCCAGTTCGCGCACGACCATCCCGAG
AAAAGGCCCCTCAGAGAGCCGCCAACCCAGTGGCGGGTCAAGCGCGTGCTGGTAGGGCTC
 F   S   G   E   S   L   G   G   W   V   T   A   Q   F   A   H   D   H   P   E
```

Fig. 4I

```
        5110                    5130                    5150
          .                       .                       .
AAGGTCGACCGGATCGTGCTCAACACCATGGGCGGCACCATGGCCAACCCTCAGGTGATG
TTCCAGCTGGCCTAGCACGAGTTGTGGTACCCGCCGTGGTACCGGTTGGGAGTCCACTAC
 K  V  D  R  I  V  L  N  T  M  G  G  T  M  A  N  P  Q  V  M 5170                    5190                    5210
          .                       .                       .
GAACGTCTCTATACCCTGTCGATGGAAGCGGCGAAGGACCCGAGCTGGGAACGCGTCAAA
CTTGCAGAGATATGGGACAGCTACCTTCGCCGCTTCCTGGGCTCGACCCTTGCGCAGTTT
 E  R  L  Y  T  L  S  M  E  A  A  K  D  P  S  W  E  R  V  K 5230                    5250                    5270
          .                       .                       .
GCACGCCTCGAATGGCTCATGGCCGACCCGACCATGGTCACCGACGACCTGATCCGCACC
CGTGCGGAGCTTACCGAGTACCGGCTGGGCTGGTACCAGTGGCTGCTGGACTAGGCGTGG
 A  R  L  E  W  L  M  A  D  P  T  M  V  T  D  D  L  I  R  T 5290                    5310                    5330
          .                       .                       .
CGCCAGGCCATCTTCCAGCAGCCGGATTGGCTCAAGGCCTGCGAGATGAACATGGCACTG
GCGGTCCGGTAGAAGGTCGTCGGCCTAACCGAGTTCCGGACGCTCTACTTGTACCGTGAC
 R  Q  A  I  F  Q  Q  P  D  W  L  K  A  C  E  M  N  M  A  L 5350                    5370                    5390
          .                       .                       .
CAGGACCTCGAAACCCGCAAGCGGAACATGATCACCGACGCCACTCTCAACGGCATCACG
GTCCTGGAGCTTTGGGCGTTCGCCTTGTACTAGTGGCTGCGGTGAGAGTTGCCGTAGTGC
 Q  D  L  E  T  R  K  R  N  M  I  T  D  A  T  L  N  G  I  T 5410                    5430                    5450
          .                       .                       .
GTGCCCGCGATGGTGCTGTGGACCACCAAGGACCCCTCCGGTCCGGTCGACGAAGCCAAG
CACGGGCGCTACCACGACACCTGGTGGTTCCTGGGGAGGCCAGGCCAGCTGCTTCGGTTC
 V  P  A  M  V  L  W  T  T  K  D  P  S  G  P  V  D  E  A  K 5470                    5490                    5510
          .                       .                       .
CGCATCGCCTCCCACATCCCGGGCGCCAAGCTGGCCATCATGGAGAACTGTGGCCACTGG
GCGTAGCGGAGGGTGTAGGGCCCGCGGTTCGACCGGTAGTACCTCTTGACACCGGTGACC
 R  I  A  S  H  I  P  G  A  K  L  A  I  M  E  N  C  G  H  W 5530                    5550                    5570
          .                       .                       .
CCCCAGTACGAGGACCCCGAGACCTTCAACAAGCTGCATCTGGACTTCCTCCTCGGTCGC
GGGGTCATGCTCCTGGGGCTCTGGAAGTTGTTCGACGTAGACCTGAAGGAGGAGCCAGCG
 P  Q  Y  E  D  P  E  T  F  N  K  L  H  L  D  F  L  L  G  R 5590                    5610                    5630
          .                       .                       .
AGCTGACACAGACCCCGGCCGGTGCCGCCAACCCCTGCAACCCGGGCGGCACCGGCCGGA
TCGACTGTGTCTGGGGCCGGCCACGGCGGTTGGGGACGTTGGGCCCGCCGTGGCCGGCCT
 S  *

5650                    5670                    5690
          .                       .                       .
TCTCACTTACCCGACCTATTGCGCTCTCGTCCGGACCCCCGGAGAGAAAGCGCCGAAGCA
AGAGTGAATGGGCTGGATAACGCGAGAGCAGGCCTGGGGGCCTCTCTTTCGCGGCTTCGT 5710                    5730                    5750
          .                       .                       .
GCAGCAAGGAGACCGCCGCGATGCCTGTAGCGCTGTGCGCGATGTCGCACTCCCCCCTGA
```

```
               CGTCGTTCCTCTGGCGGCGCTACGGACATCGCGACACGCGCTACAGCGTGAGGGGGGACT
                                M  P  V  A  L  C  A  M  S  H  S  P  L  M
           5770                5790                5810

Fig. 4J    TGGGACGCAACGACCCCGAACAGGAAGTCATCGACGCCGTCGACGCCGCATTCGACCACG
           ACCCTGCGTTGCTGGGGCTTGTCCTTCAGTAGCTGCGGCAGCTGCGGCGTAAGCTGGTGC
            G  R  N  D  P  E  Q  E  V  I  D  A  V  D  A  A  F  D  H  A
           5830                5850                5870

CGCGCCGGTTCGTCGCCGACTTCGCCCCCGATCTCATCGTCATCTTCGCCCCCGACCACT
           GCGCGGCCAAGCAGCGGCTGAAGCGGGGGCTAGAGTAGCAGTAGAAGCGGGGGCTGGTGA
            R  R  F  V  A  D  F  A  P  D  L  I  V  I  F  A  P  D  H  Y
           5890                5910                5930

ACAACGGCGTCTTCTACGACCTGCTGCCGCCGTTCTGTATCGGTGCCGCCGCGCAGTCCG
           TGTTGCCGCAGAAGATGCTGGACGACGGCGGCAAGACATAGCCACGGCGGCGCGTCAGGC
            N  G  V  F  Y  D  L  L  P  P  F  C  I  G  A  A  A  Q  S  V
           5950                5970                5990

TCGGCGACTACGGCACCGAAGCCGGCCCTCTCGACGTCGACCGTGACGCCGCCTACGCAG
           AGCCGCTGATGCCGTGGCTTCGGCCGGGAGAGCTGCAGCTGGCACTGCGGCGGATGCGTC
            G  D  Y  G  T  E  A  G  P  L  D  V  D  R  D  A  A  Y  A  V
           6010                6030                6050

TCGCCCGCGACGTCCTCGACAGCGGCATCGACGTCGCATTCTCCGAACGCATGCACGTCG
           AGCGGGCGCTGCAGGAGCTGTCGCCGTAGCTGCAGCGTAAGAGGCTTGCGTACGTGCAGC
            A  R  D  V  L  D  S  G  I  D  V  A  F  S  E  R  M  H  V  D
           6070                6090                6110

ACCACGGATTCGCCCAAGCACTCCAATTGCTGGTCGGATCGATCACCGCCGTGCCGACCG
           TGGTGCCTAAGCGGGTTCGTGAGGTTAACGACCAGCCTAGCTAGTGGCGGCACGGCTGGC
            H  G  F  A  Q  A  L  Q  L  L  V  G  S  I  T  A  V  P  T  V
           6130                6150                6170

TGCCGATCTTCATCAATTCGGTCGCCGAACCGCTCGGCCCGGTCAGCCGGGTACGGCTGC
           ACGGCTAGAAGTAGTTAAGCCAGCGGCTTGGCGAGCCGGGCCAGTCGGCCCATGCCGACG
            P  I  F  I  N  S  V  A  E  P  L  G  P  V  S  R  V  R  L  L
           6190                6210                6230

TCGGCGAGGCGGTCGGGCGGGCCGCTGCCAAGCTGGACAAGCGTGTGCTGTTCGTCGGAT
           AGCCGCTCCGCCAGCCCGCCCGGCGACGGTTCGACCTGTTCGCACACGACAAGCAGCCTA
            G  E  A  V  G  R  A  A  A  K  L  D  K  R  V  L  F  V  G  S
           6250                6270                6290

CCGGCGGCCTGTCCCACGACCCGCCGGTCCCGCAGTTCGCCACCGCGCCAGAGGAAGTGC
           GGCCGCCGGACAGGGTGCTGGGCGGCCAGGGCGTCAAGCGGTGGCGCGGTCTCCTTCACG
            G  G  L  S  H  D  P  P  V  P  Q  F  A  T  A  P  E  E  V  R
           6310                6330                6350

GCGAGCGGTTGATCGACGGCCGCAATCCCAGTGCCGCCGAACGTGATGCCCGCGAACAGC
           CGCTCGCCAACTAGCTGCCGGCGTTAGGGTCACGGCGGCTTGCACTACGGGCGCTTGTCG
            E  R  L  I  D  G  R  N  P  S  A  A  E  R  D  A  R  E  Q  R
```

Fig. 4K

```
              6370                    6390                  6410
    GCGTCATCACCGCCGGGCGGGACTTCGCCGCCGGCACCGCCGCCATCCAGCCACTGAACC
    CGCAGTAGTGGCGGCCCGCCCTGAAGCGGCGGCCGTGGCGGCGGTAGGTCGGTGACTTGG
      V  I  T  A  G  R  D  F  A  A  G  T  A  A  I  Q  P  L  N  P 6430                    6450                  6470
    CCGAATGGGACCGGCACCTGCTCGACGTCCTCGCCTCCGGCGACCTCGAGCAGATCGACG
    GGCTTACCCTGGCCGTGGACGAGCTGCAGGAGCGGAGGCCGCTGGAGCTCGTCTAGCTGC
      E  W  D  R  H  L  L  D  V  L  A  S  G  D  L  E  Q  I  D  A 6490                    6510                  6530
    CGTGGACCAACGACTGGTTCGTCGAACAGGCCGGACACTCCTCCCACGAAGTGCGCACCT
    GCACCTGGTTGCTGACCAAGCAGCTTGTCCGGCCTGTGAGGAGGGTGCTTCACGCGTGGA
      W  T  N  D  W  F  V  E  Q  A  G  H  S  S  H  E  V  R  T  W 6550                    6570                  6590
    GGATCGCCGCGTACGCGGCAATGAGCGCCGCCGGGAAGTACCGCGTCACCTCGACCTTCT
    CCTAGCGGCGCATGCGCCGTTACTCGCGGCGGCCCTTCATGGCGCAGTGGAGCTGGAAGA
      I  A  A  Y  A  A  M  S  A  A  G  K  Y  R  V  T  S  T  F  Y 6610                    6630                  6650
    ACCGCGAAATCCACGAGTGGATAGCAGGATTCGGGATTACTACCGCCGTCGCCGTCGACG
    TGGCGCTTTAGGTGCTCACCTATCGTCCTAAGCCCTAATGATGGCGGCAGCGGCAGCTGC
      R  E  I  H  E  W  I  A  G  F  G  I  T  T  A  V  A  V  D  E 6670                    6690                  6710
    AATAGACCCCGCCGCTCCCGCCCCGCAGTCCCAACGAAGGGTGGCCCCGGATGACCTCCG
    TTATCTGGGGCGGCGAGGGCGGGGCGTCAGGGTTGCTTCCCACCGGGGCCTACTGGAGGC
      *                                            M  T  S  V 6730                    6750                  6770
    TCCGCCCGTGCTCGCCGTCGGTGAACGCGGGCTGGTCGGTGGGCAGGAAGACCTCATCGC
    AGGCGGGCACGAGCGGCAGCCACTTGCGCCCGACCAGCCACCCGTCCTTCTGGAGTAGCG
      R  P  C  S  P  S  V  N  A  G  W  S  V  G  R  K  T  S  S  P 6790                    6810                  6830
    CGACATCGCCCTCGACCTCGCAGCTCGTCAGTAGGAATGCGCACGGGCCGACGAGTCGCG
    GCTGTAGCGGGAGCTGGAGCGTCGAGCAGTCATCCTTACGCGTGCCCGGCTGCTCAGCGC
      T  S  P  S  T  S  Q  L  V  S  R  N  A  H  G  P  T  S  R  A 6850                    6870                  6890
    CTGGTCACCGGGGCCAGCCGCGGCATCGGGGCGGCCATCGCAGATGCGGTGGCCGCCTCC
    GACCAGTGGCCCCGGTCGGCGCCGTAGCCCCGCCGGTAGCGTCTACGCCACCGGCGGAGG
      G  H  R  G  Q  P  R  H  R  G  G  H  R  R  C  G  G  R  L  R 6910                    6930                  6950
    GGTGCCGCCGTAATCGTCCACTACGGATCCGATCGGACGGCCGCCGCTGCGGTGTCGACG
    CCACGGCGGCATTAGCAGGTGATGCCTAGGCTAGCCTGCCGGCGGCGACGCCACAGCTGC
      C  R  R  N  R  P  L  R  I  R  S  D  G  R  R  C  G  V  D  G 6970                    6990                  7010
    GCATCACGGCTGCCGGGGGCCTCGCGGCTGCGGTCCAGGCCGACCTGTCCCGACCCGAGG
```

Fig. 4L

```
      CGTAGTGCCGACGGCCCCCGGAGCGCCGACGCCAGGTCCGGCTGGACAGGGCTGGGCTCC
        I  T  A  A  G  G  L  A  A  A  V  Q  A  D  L  S  R  P  E  G 7030               7050               7070

GGCCTGAAGAGCTGATGCGGGAGTTCGACTCCGCGCTCGACGGTCTCGGGCTCGACCGAG
      CCGGACTTCTCGACTACGCCCTCAAGCTGAGGCGCGAGCTGCCAGAGCCCGAGCTGGCTC
        P  E  E  L  M  R  E  F  D  S  A  L  D  G  L  G  L  D  R  G 7090               7110               7130

GGCTCGACATCCTCGTCAACAACGCCGGAATCAGTCGGCGCGGAGCGCTCGAGCGCGTCA
      CCGAGCTGTAGGAGCAGTTGTTGCGGCCTTAGTCAGCCGCGCCTCGCGAGCTCGCGCAGT
        L  D  I  L  V  N  N  A  G  I  S  R  R  G  A  L  E  R  V  T 7150               7170               7190

.CTGTCGAGGATTTCGACCGTCTGGTCGCACTCAACCAGCGCGCCCCGTTCTTCGTGACTC
       GACAGCTCCTAAAGCTGGCAGACCAGCGTGAGTTGGTCGCGCGGGGCAAGAAGCACTGAG
         V  E  D  F  D  R  L  V  A  L  N  Q  R  A  P  F  F  V  T  R 7210               7230               7250

GGCATGCCCTGCCCCGGATGCACGACGGCGGTCGCATCGTCAACATTTCCTCCGGATCCG
      CCGTACGGGACGGGGCCTACGTGCTGCCGCCAGCGTAGCAGTTGTAAAGGAGGCCTAGGC
        H  A  L  P  R  M  H  D  G  G  R  I  V  N  I  S  S  G  S  A 7270               7290               7310

CCCGCTACGCCAGACCCGACGTCATCAGCTACGCCATGACCAAGGGGGCGATCGAGGTGC
      GGGCGATGCGGTCTGGGCTGCAGTAGTCGATGCGGTACTGGTTCCCCCGCTAGCTCCACG
        R  Y  A  R  P  D  V  I  S  Y  A  M  T  K  G  A  I  E  V  L 7330               7350               7370

TCACCCGCGCCCTCGCCGTAGACGTCGGCGAACGAGGCATCACCGCCAACGCCGTGGCGC
      AGTGGGCGCGGGAGCGGCATCTGCAGCCGCTTGCTCCGTAGTGGCGGTTGCGGCACCGCG
        T  R  A  L  A  V  D  V  G  E  R  G  I  T  A  N  A  V  A  P 7390               7410               7430

CGGCCGCGCTCGATACCGACATGAACGCGCACTGGCTTCGCGGTGACGACCATGCCCGCA
      GCCGGCGCGAGCTATGGCTGTACTTGCGCGTGACCGAAGCGCCACTGCTGGTACGGGCGT
        A  A  L  D  T  D  M  N  A  H  W  L  R  G  D  D  H  A  R  T 7450               7470               7490

CCACCGCCGCGTCCACCACTGCACTGCGAAAACTCGCCACCGCGGAGGACATCGCCGCGA
      GGTGGCGGCGCAGGTGGTGACGTGACGCTTTTGAGCGGTGGCGCCTCCTGTAGCGGCGCT
        T  A  A  S  T  T  A  L  R  K  L  A  T  A  E  D  I  A  A  I 7510               7530               7550

TCGTGGCCTTCCTCGTCAGCGCCGCCGCCGGTGCGATCACCGGGCAGGTCATCGACGCCA
      AGCACCGGAAGGAGCAGTCGCGGCGGCGGCCACGCTAGTGGCCCGTCCAGTAGCTGCGGT
        V  A  F  L  V  S  A  A  A  G  A  I  T  G  Q  V  I  D  A  T

7570

CCAACGGCAACCGGCTCTAACCAG
      GGTTGCCGTTGGCCGAGATTGGTC
        N  G  N  R  L  *
```

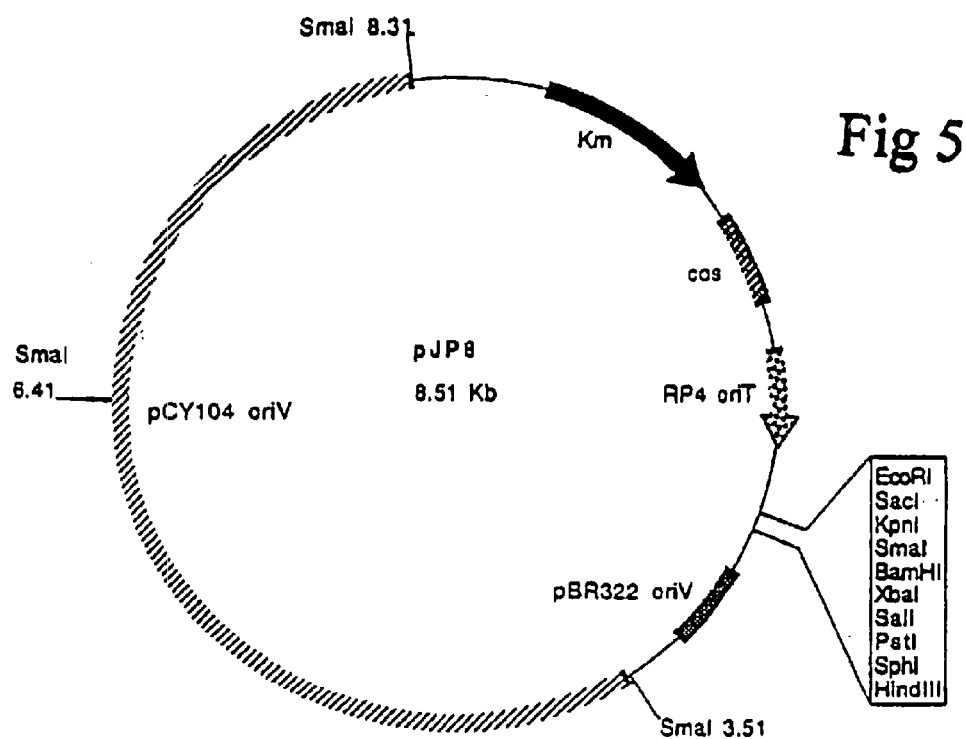

BIOSENSOR MATERIALS AND METHODS

TECHNICAL FIELD

This invention relates to biosensor materials and methods, and in particular to methods for generating microorganisms having utility in biosensing, tools which can be generally used in such methods, the microorganisms themselves, and biosensing methods employing such microorganisms.

BACKGROUND ART

It is frequently desirable to be able to detect small concentrations of analytes in samples, e.g. environmental samples. For instance, to allow more effective management of scarce environmental resources, more efficient and faster methods of assessing environmental pollution are required. At present, molecular-specific monitoring of effluent streams and other environmental matrices requires extensive chemical manipulation of the sample followed by Gas Chromatography (GC) and Mass Spectrometry (MS) analyses. Although these techniques are highly sensitive, sample preparation is necessarily slow and expensive. Consequently, continuous on-site analysis of a variety of environmental matrices cannot be achieved using these methods at reasonable cost.

An alternative method for the determination of phenols and chlorophenols has been proposed using a biosensor based around *Rhodococcus* sp. [see Riedel et al (1993) Appl microbiol Biotechnol 38: 556–559]. In this method microorganisms are immobilised in an oxygen electrode, and oxygen uptake in response to added substrates was monitored. Although fairly simple and rapid, this method lacks robustness and is not sufficiently sensitive or specific for detecting particular environmental pollutants.

It can thus be seen that the provision of novel materials and methods capable of being used in the field of biosensing would represent a step forward in the art.

DISCLOSURE OF INVENTION

In a first aspect of the invention there is disclosed a method of detecting the presence or absence of an analyte in a sample comprising the steps of:
(a) contacting the sample with a transformed microorganism which is a mycolic acid bacterium which expresses a binding agent capable of binding the analyte, wherein the binding of the agent to the analyte causes a detectable signal, and wherein said bacterium has been transformed such as to improve the detectability of the signal; and
(b) observing said bacterium for said detectable signal;

By "observing" is meant ascertaining by any means (directly or indirectly) the presence or absence of the selected signal which is indicative of the binding event.

By "improve" is meant, inter alia, altering the nature of the signal to one which can be observed more readily or increasing the intensity of the signal (thereby reducing the sensitivity of the means used to observe it).

Thus by using a transformed microorganism, the limitations inherent in wild-type microorganisms such as those used in the prior art may be overcome. In particular more sensitive and robust monitoring methods than those based on natural biochemical activities such as oxygen uptake can be employed. The mycolic acid bacterial gene expression-based sensors of the present invention can combine high sensitivity with the biofiltering and bioconcentrating aspects of the mycolic acid bacterial cell wall. Methods for generating such transformants are described in further detail below. Such transformed microorganisms are hereinafter referred to as 'biosensors'.

Preferably the analyte is an environmental pollutant, for instance such as may result from industrial or medical applications. Of particular interest is the detection of mono- and poly-aromatic, cyclic, heterocyclic and linear hydrocarbons such as, but not limited to, components of fuels, solvents, propellants, energetics and pesticides (such as may appear on United States EPA Priority Pollutants List and European Community Grey and Black Lists) and naturally occurring degradation products of these compounds in industrial process media, vapours, effluents, raw water, rivers, ground waters, or soils. As will be clear to the skilled person from the disclosure hereinafter, the methodology of invention is inherently flexible and may, in principle, be employed to develop mycolic bacteria capable of biosensing almost any target analyte.

The mycolic acid bacteria form a supra generic group of Gram-positive, non-sporulating bacteria which is comprised of the genera *Corynebacterium, Mycobacterium, Nocardia, Rhodococcus, Gordona, Dietzia* and *Tsukamurella*. Members are metabolically diverse and capable of using as sole carbon source (a growth-inducing substrate) a wide range of natural and xenobiotic compounds, including many key environmentally-toxic and/or industrially-important molecules e.g. hydrophic organic compounds. The mycolic acid bacteria exhibit several structural and physiological features which appear to be specialisations for hydrocarbon degradation, these include a hydrophobic mycolic acid outer cell layer and associated production of extracellular mycolic acid-derived biosurfactants. Most preferably the bacterium is a member of the *Rhodococcus* or *Nocardia* complex (i.e. nocardioform actinomycete).

The detectable signal may be a change in enzyme function (s), metabolic function(s) or gene expression.

Preferably however the signal is ascertained in consequence to an increased expression of a signal protein from a signal gene, more preferably a heterologous signal gene. Many suitable signal proteins (which have a readily detectable activity) are known in the art e.g. βgalactosidase, which can generate a coloured substrate. The signal may utilise co-factors. Most preferably the activity of the signal protein, or the protein itself, can be estimated photometrically (especially by fluorimetry). This may be directly e.g. using instance green (and red) fluorescent protein, insect luciferase, and photobacterial luciferase. Alternatively it may be indirect e.g. whereby the signal gene causes a change which is detected by a colour indicator e.g. a pH change. Methods for introducing signal genes into appropriate hosts are described in further detail below.

Generally the bound agent/analyte complex will initiate expression of a signal gene which is operably linked to an inducible promoter. The identification of suitable promoters and/or coding sequences which are operably linked to them (including that of the binding protein) in mycolic acid bacteria, in order to modify said suitable promoters and/or coding sequences to introduce signal genes therein forms one part of the present invention.

As used herein, "promoter" refers to a non-coding region of DNA involved in binding of RNA polymerase and other factors that initiate or modulate transcription from a coding region of DNA whereby an RNA transcript is produced.

An "inducible" promoter requires specific signals in order for it to be turned on or off.

The terms "operatively linked" and "operably linked" refer to the linkage of a promoter to an RNA-encoding DNA sequence, and especially to the ability of the promoter to induce production of RNA transcripts corresponding to the DNA sequence when the promoter or regulatory sequence is recognized by a suitable polymerase. The term means that linked DNA sequences (e.g., promoter(s), structural gene (e.g., reporter gene(s)), terminator sequence(s), are operational or functional, i.e. work for their intended purposes.

As is known to those skilled in the art, the transport and binding proteins (agents) required for the functionality of the inducible promoter, as well as the catabolic enzymes induced by it, will frequently form part the operon containing the promoter, and may thus be identified and isolated along side it using the methods disclosed above. These additional proteins are hereinafter referred to as "operon proteins".

Generally speaking, those skilled in the art are well able to construct vectors and design protocols for recombinant gene expression in common hosts such as *E. coli*. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

However, the present inventors have recognised that certain methods previously employed in the art which were developed for enteric bacteria such as *E. coli* may not be the most appropriate for use in mycolic acid bacteria. The mycolic acid layer and associated biosurfactants (which are a defining feature of these bacteria) and thick cell wall confer great resistance to cell lysis protocols known in the art. Similarly, mycolic strains used in the invention may not (indeed generally will not) be laboratory type strains, and may thus exhibit very high levels of nuclease activity.

In addition the detailed chemistry of the inducible pathway which forms the basis of the biosensors of the present invention will frequently not be known e.g. if there are no known enzyme pathways leading to the degradation of a particular analyte, or possibly the analyte is not mineralised completely and is only partially utilised in an uncharacterised but inducible pathway. Therefore cloning by acquisition of some defined enzyme activity, assayed through a particular reaction (as opposed to a general phenotypic activity which results in gain of utilisation of a particular analyte as a source of metabolically useful products) may not be a plausible option to isolate genes from a wild type mycolic acid bacterium.

Accordingly, advantageous methods have been developed by the inventors which in preferred forms allow the rapid isolation and characterisation of promoters and operably linked operon proteins which avoid or at least minimise host restriction and requires no prior knowledge of the inducible enzyme chemistry involved. The methods of identifying, modifying and employing novel inducible promoters and/or coding regions operably linked to them which are appropriate to mycolic acid bacteria are detailed below.

Thus in a second aspect of the invention there is disclosed a method for identifying DNA encoding an inducible promoter which is induced in response to a specific analyte and/or identifying DNA encoding associated operon proteins comprising the steps of:
(a) culturing a source of mycolic acid bacteria in a selective medium containing said specific analyte and being selective for oligotrophic bacteria,
(b) identifying bacteria capable of subsisting on said medium,
(c) extracting DNA from said bacteria
(d) incorporating said DNA into vectors
(e) cloning said vectors into a suitable host cells
(f) screening the host cells for said inducible promoter and/or proteins in order to identify vectors encoding it.

By "screening" is meant subjected to analysis in order to determine the presence or absence of a particular defined property or constituent. Generally, in order to construct a biosensor strain against a particular analyte, isolation de novo from the soil or other environmental matrices of mycolic acid bacteria which exhibit inducible expression of catabolic genes in the presence of the analyte will be required. Methods of screening are discussed in more detail below.

As is known to those skilled in the art "oligotrophic bacteria" are bacteria which exhibit a preference for, and persistent slow growth on, very low levels of bioavailable carbon sources. These bacteria are adapted to and predominate in carbon-poor environments (predominantly aquatic habitats where carbon is limiting to $\mu$M levels). The term as used herein is intended also to embrace those bacteria which are capable of growing on defined minimal media without supplementary amino acids and vitamins (sometime termed prototrophic). Such bacteria are rarely capable of the very rapid growth as exemplified by the enteric bacterium *E. coli*, but are by contrast, extremely persistent and metabolically versatile. Work done by the present inventors has shown that, generally speaking, auxotrophic bacteria are not suitable as biosensor strains for environmental and industrial use.

Preferably the medium used in the second aspect is a defined minimal medium called hereinafter 'MMRN' which has been developed by the present inventors to screen for the oligotrophic mycolic acid bacteria (especially rhodococcal and nocardial strains) which form the basis of the biosensor. This medium preparation is a derivative of von der Osten et al. (1989) but for mycolic acid bacteria sodium citrate and biotin are omitted. Most importantly, the level of carbon supplement is reduced to oligotrophic levels (<500 $\mu$M, more preferably <100 $\mu$M). Experiments show that MMRN facilitates simple, selective enrichment for oligotrophic, mycolic acid-containing bacteria as well as providing the basis for testing and characterisation of gene induction. The medium forms a third aspect of the present invention.

DNA may be extracted from the bacteria by any methods known in the art. However, the present inventors have demonstrated that DNA isolation from mycolic acid soil bacteria (particularly novel isolates which are generally highly resistant to lysis) using standard techniques is inefficient. Accordingly, several optimised methods of generating total DNA from mycolic bacteria have been developed, as described in more detail below (Examples 3 and 4). These involve bacterial culture in MMRN supplemented with L-glycine, oligotrophic levels of carbon source (80 $\mu$M) and removal of biosurfactants by washing in a non-ionic detergent (e.g. Tween 80) prior to a modified alkaline lysis technique. The concept of using a non-ionic detergent at between 0.05–0.5% (preferably 0.1%) in order to facilitate DNA extraction is central to the novel, optimised methods.

"Vector", unless further specified, is defined to include, inter alia, any plasmid DNA, lysogenic phage DNA and/or transposon DNA, in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication).

Preferably the host used is *E. coli*. More preferably it is an *E. coli* strain carrying one or more of the mcrABC mrr hsdSRM recA and recO mutations, since this is believed to enhance clone recovery when using DNA derived from mycolic acid bacteria which (e.g. in *Rhodococcus/Nocardia*) is GC rich. Gene libraries may be readily maintained in these strains.

Preferably the vector used with *E. coli* further incorporates the 'cos' element (which is well known to those skilled in the art). Because of their capacity and selection for large DNA inserts and efficient transfection rates, cosmid cloning vectors facilitate rapid gene library construction, which is especially useful in the present context because the activities of interest are often encoded by closely lined genes or operons which may be contained on relatively large fragments of the e.g. *Rhodococcus/Nocardia* genome.

Preferably the mycolic acid bacteria isolates are further screened, for instance after stage (b), to ensure an absence of catabolic repression. Catabolite repression is the selective control of gene expression in response to the energy state of the cell. This process is part of a range of gene expression strategies grouped under the "stringent/relaxed" responses. Together, these allow bacteria to optimise their metabolism for maximum energy efficiency. At the genetic level, catabolite repression is achieved by the selective expression of one of several sigma factors, each expressed under a different physiological state and/or growth phase (Fujita et al, 1994) each recognising a different promoter sequence (Bashyam et al, 1996). This facilitates the selective expression or repression of a wide range of genes and operons simultaneously via the regulation of a single gene product.

To create an efficient, functional biosensor, such media-associated repression/activation phenomena must be absent or be disabled in the host strain since, in principle, catabolite repression could seriously compromise the activity of a biosensor because the presence of a more efficient carbon source (such as glucose, succinate or acetate etc.) would lead to repression of hydrocarbon catabolic pathways which forms the basis of the sensor. Mycolic acid bacteria *Brevibacterium* (Oguiza et al., 1996), *Corynebacterium, Nocardia* (Takahashi, et al, 1991), *Mycobacterium smegmatis, M. Tuberculosis*, and *M. bovis* BCG (Bashyam et al, 1996) and *M. leprae* (Doukhan et al, 1995) encode multiple sigma factor genes consistent with global stringent/relaxed genetic control. Consistent with these data, catabolite repression has been experimentally observed in *Rhodococcus* (Baryshnikova, et al, 1997).

To identify strains lacking catabolic repression, the concentrations of an enzyme known to be, or suspected of being, associated with the catabolic pathway of interest (e.g. catechol 2,3-dioxygenase, which is associated with toluene catabolism) is assessed in (a) selective medium supplemented with the specific analyte, (b) selective medium supplemented with the specific analyte plus a high efficiency carbon source such as glucose (1 mM) and (c) selective medium supplemented with glucose (1 mM) alone. Enzyme activities should be very low or undetectable in the absence of analyte. In the presence of analyte, and glucose plus analyte, the activities should be, within experimental error, very similar. To ensure that not only are biosensor strains free from all complex media-associated repression/activation effects, microbiological screenings are preferably extended to include several complex media. e.g. Lauria Bertini broth or Nutrient Agar in addition to MMR+1 mM levels of individual carbon sources.

The present inventors have established that catabolic genes in mycolic acid bacteria exhibit poor DNA sequence conservation with analogous enzyme genes in Gram negative bacteria. As a result, "reverse genetic" approaches to isolation of novel catabolic pathways are likely to be of limited use when using such published sequence data.

Thus in one embodiment of the second aspect, the host cells are screened for the inducible promoter and/or operon proteins by screening the cells using one or more probes based on the sequence of other promoters and/or operon proteins employed by mycolic acid bacteria in catabolic enzyme production. One example of a source of suitable sequences is the promoter operator region of the *R. corallina* orthohydroxyphenylpropionic—ohp—acid catabolic operon (which we had previously designated the moncaromatic catabolic—mac—operon) the sequence of which has been made available by the present inventors for the first time. This is described in more detail below, and in Example 9. Thus an inducible promoter and/or operon proteins may be identified by providing a nucleic acid molecule having a nucleotide sequence identical to, complementary to, or specifically hybridisable with, the corresponding part of a known, appropriate, mycolic acid bacterial sequence, such as the sequence shown in FIG. 4. Preferably parts of the sequence are used as probes, preferably of at least 100 nucleotides (but shorter sequences may be employed under high stringency conditions). The use of primers based on the sequence to screen and identify target sequences by PCR is also envisaged.

The identified putative inducible promoter can then be tested to see if it is operational as described in more detail below. Briefly, the putative promoter is provided in a vector upstream of a protein coding sequence (e.g. a reporter gene) at a position in which it is believed to be operatively linked to that coding sequence. A suitable host is transformed with the resulting vector. The presence or absence of the coding sequence expression product, in the presence of the inducing molecule, is determined. For putative transport proteins or catabolic enzymes identified by homology, function can be confirmed as described below.

As an alternative, or in addition to, homology screening, operon proteins which have catabolic enzymic activity can be screened for by their activity. For instance by contacting substrates for the enzymes (the analytes) with the host cells, or extracts therefrom, and observing for degradation products.

This approach can be used when the enzyme concerned may be successfully expressed in the recombinant host cell. For example, the *R. corallina* ohp operon was isolated by screening recombinant *E. coli* for expression of a catechol 2,3-dioxygenase activity induced in *R. corallina* when grown on monoaromatic compounds such as toluene. The substrate of this enzyme is catechol, a water soluble 2 hydroxyphenol which does not lyse *E. coli*.

In fact, *R. corallina* does express a mac catechol 2,3-dioxygenase activity in the presence of toluene. However that activity was not isolated in *E. coli*. Instead, the ohp-associated catechol 2,3-dioxygenase activity was isolated. This enzyme is induced by orthohydroxyphenylpropionic acid in the medium, although it does cleave catechol. A likely reason for the isolation of the ohp enzyme (rather than the mac one) is that functional screening in *E. coli*, even in those cases where it is possible, will depend not only on the requisite activity being expressed by the host, but also on the relative efficiency with which it is expressed. Thus using *E. coli* as the host, and using a broadly specific enzyme screen, those genes from nocardioform actinomycetes which are most efficiently expressed will be preferentially isolated.

Additionally, other potential substrates/analytes e.g. toluene are highly toxic to *E. coli* and may cause its membrane to destabilise leading to cell lysis. Further, gene isolation by function is limited to those genes that are expressed in the test bacterium. Because of their evolutionary distance from the mycolic acid bacteria, established cloning hosts such as *E. coli* or Gram-positive bacteria such as *Bacillus subtilis* and *Staphylococcus aureus* may not effectively recognise mycolic acid bacterial gene regulatory signals and/or may not transport or survive in the presence or xenobiotics per se. Therefore, isolation by acquisition of novel-phenotype cannot easily be accomplished in these hosts.

In addition, when screening for proteins involved in binding or transporting the analyte, or transducing this binding event to the inducible promoter (e.g. transcription factors), it may be necessary to use a host in which other elements of the entire system (i.e. promoter and/or signal gene or catabolic enzymes) are present in order to demonstrate activity.

In order to circumvent these problems, in a most preferred embodiment of the second aspect, vectors comprising the inducible promoter and/or operon proteins are identified by means of a functional screen in a second host. This can avoid the difficulties described above. Preferably this second host is a suitable mycolic acid bacterium.

In order that the vectors can be maintained in the mycolic acid bacteria, they must encode replicons which can function in mycolic acid bacteria. These replicons can be those known in the art (e.g. based on characterised mycolic acid bacterial plasmids pSR1 (Batt et al., 1985). Alternatively the present inventors have provided a novel method of generating supercoiled or circular plasmid DNA from mycolic bacteria, and this method forms one part of the present invention. The diversity of the mycolic acid bacteria means that it is unlikely that a single replicon will be sufficient to construct biosensors in all strains encountered. Novel replicons which can be used either alone or in conjunction (two or more per vector) with other replicons to expand host range therefore provide a useful contribution to the art.

Thus, using the supercoiled/plasmid method of DNA isolation detailed in Example 4, two previously uncharacterised plasmids pRC100 and pRC158 have been discovered in soil mycolic acid bacteria *Rhodococcus corallina* and mycolic acid bacterium strain RC158 respectively.

Strain RC158 contains a supercoiled plasmid of approximately 14.57 kb. The plasmid, designated pRC158, contains at least five EcORI restriction enzyme sites which can be used to digest the plasmid into a specific restriction pattern of five major restriction fragments of 4.3, 3.3, 2.9, 2.2 and 1.6 Kb DNA respectively. An approximately 100 kb plasmid, pRC100, was isolated from *R. corallina*

Replicons may be identified from novel plasmids by screening fragments obtained therefrom in disabled vectors containing marker proteins (for instance based on pJP7 described below) to see if they can replicate in mycolic acid bacteria.

Novel plasmids isolated using the method, and novel replicon elements isolated from them, form a fourth aspect of the present invention. These, and existing replicons, may be used to construct cloning vectors which replicate in several mycolic acid bacterial strains. Thus it is possible to clone, isolate by function and express specific genes from not only a single "type strain" as is the common practice in molecular biology but also in a variety of mycolic acid bacteria.

It is preferable that the transfer of the vectors comprising the putative inducible promoters and/or operon proteins to the second host (preferably mycolic acid bacteria) from the first host (preferably an established cloning systems such as *E. coli*) be achieved using bacterial conjugation. Experiments have shown that restriction enzyme activity in newly isolated mycolic acid bacteria effectively limits the efficiency of electroporation of incorrectly methylated plasmid DNA to very low, or undetectable levels. It is known that most restriction enzymes preferentially act on double stranded DNA substrates. It is known that conjugative DNA transfer, however, involves a single-stranded DNA intermediate and is thus relatively immune to restriction. It is known that the IncPa conjugative plasmid RP4 can transfer its DNA into a wide range of bacteria by conjugation. Accordingly, a series of conjugatively mobilizable mycolic acid bacteria/*E. coli* shuttle vectors have been constructed by incorporation of a 440 bp region of the RP4 plasmid encoding the origin of transfer (pJP8 FIG. 1). Experiments have shown that RP4 oriT vectors can be complemented in trans for tra functions allowing conjugative mobilization into a variety of mycolic acid bacteria at high efficiency.

The vectors for use in the most preferred embodiment of second aspect of the invention (i.e. functional screening in a second host), themselves form a fifth aspect of the present invention, such vectors typically comprising:

(a) a replicon for mycolic acid bacteria
(b) a replicon for *E. coli*
(c) a conjugative origin of transfer
(d) a lambda cos site An example of such a vector is that termed pJP8 (FIG. 5). This comprises (a) pCY104oriV, (b) pBR322 oriV (c) RP4 oriT, and (d) a cos site; however it will be apparent to those skilled in the art that any of these could be substituted for a sequence having similar function, for instance substituting pRC100 or pRC158 minimal replicon sequences for the novel pCY104 replicon.

Further plasmids are pRV1 and pJH6 which comprise oriV (for replication in *E. coli*); oriT (for transfer); Kan (antibiotic marker); pSR1 (for replication); a cos site.

In use such vectors will further comprise a fragment containing the putative inducible promoter and/or operon proteins and optionally a signal protein, such as have been described above.

Thus a gene library can be constructed in a mobilizable cosmid shuttle vector such as pJP8. After in vitro packaging, cosmids can be recovered by adsorption to *E. coli* carrying mcrABC mrr hsdSRM recA recO. Given the size of the mycolic acid genome (approximately 4 Mb) a 99% confidence gene library requires approximately 2500 colonies.

To screen for specific functions (either a complete reaction pathway or specific reactions) the packaged cosmids may be adsorbed to *E. coli* mcrABC mrr hsdSRM recA recO containing an IncP plasmid such as RK2. Since the RK2 plasmid encodes several antibiotic resistance genes, it is modified by random mutagenesis to disable antibiotic resistance genes which are also used as markers in the cosmid vector. From this transformed strain, the mobilizable cosmid shuttle vector may be conjugated into a wide variety of mycolic acid bacteria for functional screening. In any such screen, the choice of mycolic acid bacterial strain will be governed by the known catabolic functions of the strain.

Thus entire pathways may be isolated by screening for gain of function. Alternatively, if a particular strain is known to require only one or a few catabolic activities these may be screened for by complementation.

Another novel shuttle vector, pRV1, can be recovered with high efficiency in a suitable *E. coli* host, and then transfer to a mycolic acid bacterial strain via conjugation (which minimises host restriction difficulties) for screening. Thus, in this embodiment, the *E coli* strain is just an interim host. Optionally conjugative systems can be put into place in this interim host to directly allow mating to follow phage adsorption, thus minimising the period in *E. coli.*

By incorporation of a signal gene adjacent to the cloning site in pJP8 or pRV1 used to construct the gene library, transconjugant mycolic acid bacteria can be screened for inducible expression of a signal protein such as luciferase in the presence of specific molecules. This will rapidly isolate environmentally responsive promoter/operator/regulator elements.

Once identified, by any of the methods of the second aspect of the invention above, the putative inducible promoter and/or operon proteins may be modified by subcloning mutagenesis (typically within *E. coli*) and screened for enhanced function in mycolic acid bacteria.

The term 'modified' is used to mean a sequence obtainable by introducing changes into the full-length or part-length sequence, for example substitutions, insertions, and/or deletions. This may be achieved by any appropriate technique, including restriction of the sequence with an endonuclease followed by the insertion of a selected base sequence (using linkers if required) and ligation. Also possible is PCR-mediated mutagenesis using mutant primers.

It may, for instance, be preferable to add in or remove restriction sites in order to facilitate further cloning.

Alternatively, it may be particularly desirable to modify the binding protein/agent in order to modify its specificity and/or affinity for analyte.

Modified sequences according to the present invention may have a sequence at least 70% identical to the sequence of the full or part-length inducible promoter or operon protein as appropriate. Typically there is 80% or more, 90% or more 95% or more or 98% or more identity between the modified sequence and the authentic sequence. There may be up to five, for example up to ten or up to twenty or more nucleotide deletions, insertions and/or substitutions made to the full-length or part length sequence provided functionality is not totally lost.

Modified promoters and/or operon proteins can be screened for functionality as described above in relation to isolating novel elements.

Nucleic acid encoding the authentic or modified promoter and/or genes encoding the operon proteins (plus such modified proteins themselves) identified or obtained by the method of the second aspect of the invention form a sixth aspect of the invention.

Figure 3:
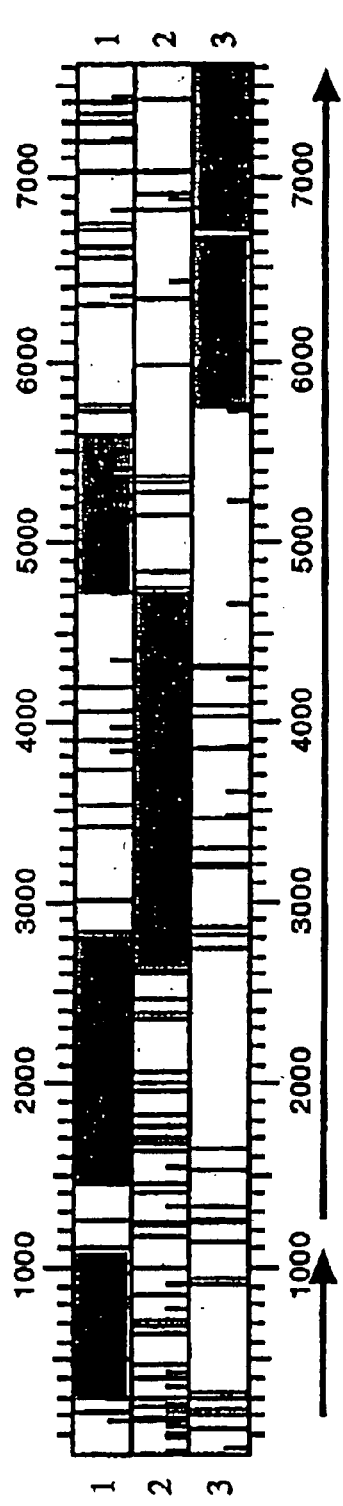

Thus one embodiment of the sixth aspect is the *R. corallina* ohp locus described in FIGS. 3 and 4 including the promoter and individual operon proteins encoding therein, and modifications thereof.

The authentic or modified promoter identified or obtained by the method of the second aspect of the invention may be used to inducibly express a heterologous signal protein in a transformed host; this use forms a seventh aspect of the present invention.

In one embodiment of the seventh aspect, there is disclosed a method of transforming a host with a vector encoding the inducible promoter as described above, operably linked to the signal gene (e.g. encoding luciferase).

The vector used in the seventh aspect may remain discrete in the host. Alternatively it may integrate into the genome of the host.

For a potential host (e.g. *Corynebacterium*) which does not express or generate the other components of the system which may be required to give biosensor function (for instance the operon proteins such as the transport protein to transport analyte into the cell; binding protein to bind analyte thereby inducing the promoter activity; cofactors required for signal protein activity etc.) these components can be added exogenously in order to perform the methods of the first aspect, or can be encoded on the vector used to introduce the inducible promoter or supplied in trans on a separate nucleic acid. Indeed, as stated above, any transport and binding proteins required for the functionality of the inducible promoter will frequently form part the operon containing the promoter, and may thus be identified and isolated alongside it using the methods disclosed above.

Preferably, however, the host (e.g. a mycolic acid bacterium, either the same or different to that which provided the source of the inducible promoter, but preferably the same) will itself naturally express the other components of the system required to give biosensor function. This ensures all the required gene products for biosensor function are present.

Indeed in this latter case, the signal protein gene may be introduced into the host such that it is operably linked to an existing inducible promoter. In this embodiment of the seventh aspect of the invention the identification and or isolation of the promoter or associated proteins as described above ultimately provides the information required to allow targeting of the gene into this region. Typically this will be achieved by initiating targeted integration using aspects of the sequence forming part of the promoter region or operon.

Direct integration of a signal gene system such as luciferase (e.g. luxAB operon) into an environmentally responsive regulon in a mycolic acid containing bacterium may be more efficient than approaches based on isolation of gene(s) and its/their characterisation followed by construction of the biosensor. This integration can be achieved by transposition or by illegitimate or legitimate recombination between a genetic construct introduced into the cell and the target operon or gene cluster located on either the chromosome or an episomal element. In situations where a gene cluster or operon has been identified as above, by either screening in *E. coli* or direct functional cloning in a mycolic acid bacterium, site-specific recombination may be used to direct integration of the signal gene(s) (such as luciferase) into the regulon.

Vectors for use in the seventh aspect of the invention, form an eighth aspect of the invention. Such vectors will typically include: (a) the signal gene, plus (b) the inducible promoter, operably linked to the signal gene, or a sequence capable of initiating recombination of the signal gene such that it becomes operably linked with the inducible promoter. Further operon proteins (optionally modified) may also be included in the vector.

Vectors of the eighth aspect of the invention can be readily constructed on the basis of the present disclosure, for instance based on pJP7 (FIG. 6) which is described in more detail below.

Strain derivatives encoding different gene dosage levels of the promoter/signal gene can be created by integration of the construct into the chromosome (low copy number/low sensitivity) or by use of medium or high copy number plasmids (medium or high sensitivity).

A ninth aspect of the invention is a (biosensor) host transformed with the vectors of the eighth aspect.

In using the transformants of the ninth aspect in the methods of the first aspect, the signal (such as bacterial luciferase) may be detected extracellularly using a photomultiplier or photodiode or any other photosensitive device. This maintains the cell integrity and thus resistance to environmental shock.

Also embraced within the scope of the present invention are kits for performing the various aspects of the invention. For instance a kit suitable for use in the first aspect may comprise a preparation of the microorganism, plus further means for carrying out the contact or observation steps e.g. buffers, co-factors (e.g. luciferin for addition to luciferase). A kit for performing the second aspect may include any of the following: selective buffer, a non-ionic detergent, any means for carrying out the screening process (e.g. primers, probes, substrates for catabolic enzymes, vectors for transfer into a second host). Kits for performing the seventh aspect may include vectors for generating biosensors plus other means for transforming hosts with them (e.g. buffers etc.).

The invention will now be further described with reference to the following non-limiting Figures and Examples. Other embodiments falling within the scope of the present invention will occur to those skilled in the art in the light of these.

FIGURES

FIG. 1—shows an agarose gel on which digestions of the novel plasmid pRC100 has been run, as described in Example 5.

Figure 2:
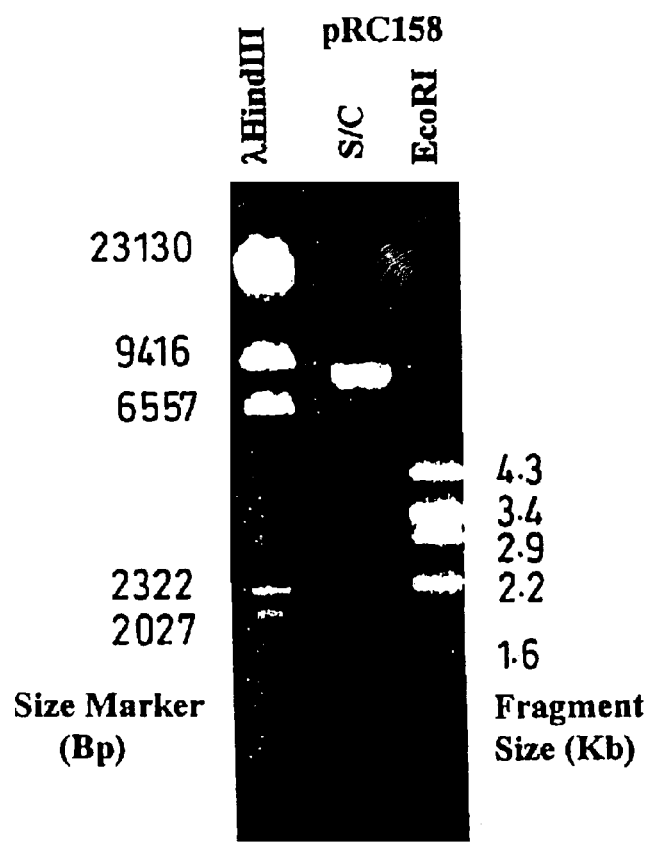

FIG. 2—shows an agarose gel on which digestions of the novel plasmid pRC158 has been run, as described in Example 5.

FIG. 3—shows a schematic view of the R. corallina ohp operon obtained by functional screening in E. coli, as described in Example 7. The schematic shows location of predicted genes: Regulator (SEQ ID No. 3), Transport (SEQ ID No. 4), Monooxygenase (SEQ ID No. 5), Hydroxymuconic semialdehye hydrolase (SEQ ID No. 6), Catechol-2, 3-dioxygenase (SEQ ID NO. 7), Alcohol dehydrogenase (SEQ ID No. 8). Initiator and terminator codons are shown as half height and full height lines respectively. Base coordinates refer to the FIG. 4 sequence. The location of predicted promoter regions and direction are indicated by arrows. The molecular weights and coordinates of ohp genes are tabulated.

FIGS. 4A–4L—show the complete listing of the R. corallina ohp operon as described in Example 7 (SEQ ID No. 1—top strand; SEQ ID No. 2—bottom strand). It includes a portion of a putative nitropropane promoter (5' of the regulator; amino acid sequence shown in SEQ ID No. 3).

FIG. 5—shows a schematic diagram of the pJP8 vector of the present invention, as described in Example 8. Plasmid size is about 8.51 kb. pJP8 is a mycolic acid bacterium—E. coli mobilizable cosmid vector. It carries pCY104 replicon; is Kanamycin resistant 15 μg/ml mycolic acid bacteria, 50 μg/ml E. coli. It also carries lambda cos site, RP4 oriT site and a multiple cloning site.

FIG. 6—shows a schematic diagram of the pJP7 vector of the present invention, as described in Example 9. Plasmid size is about 10.66 kb. pJP7 is a mobilizable E. coli/Rhodococcus/Nocardia suicide/luciferase integration vector encoding luxAB signal genes, sacB gene and thiostreppton resistance in Rhodococcus/Nocardia only up to 75 μg/ml (typically 1–10 μg/ml used in selections). The vector is RP4/RK2 mobilizable. By cloning a region of homology into the region upstream of the luxAB cassette, insertion can be targeted.

Figure 7:
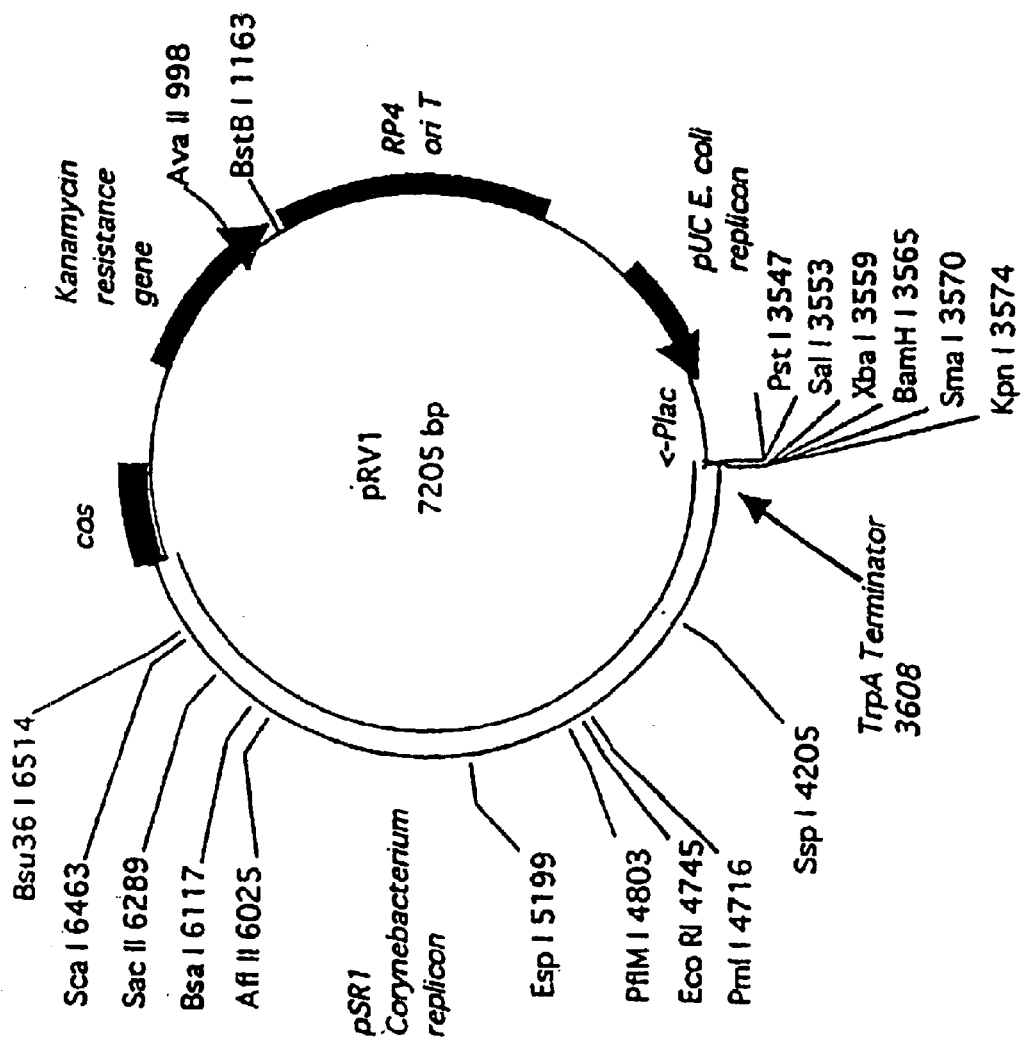

FIG. 7—shows a schematic diagram of the pRV1 vector of the present invention, as described in the Examples below. Plasmid pRV1 comprises a minimal pSR1 replicon (Archer & Sinskey, 1993 J Gen Microbiol 139: 1753–1759) which allows replication in C glutamicum. The pUC replication origin (Yanish et al, 1985 Gene 33: 103–119) allows replication in E. coli. Also included are a kanamycin resistance marker and the RP4 origin of conjugative transfer oriT. Transcription counterclockwise in the insert is terminated by the E. coli trpA terminator. Transcription clockwise into the insert may be initiated by the E. coli lac UV5 promoter.

Figure 8:
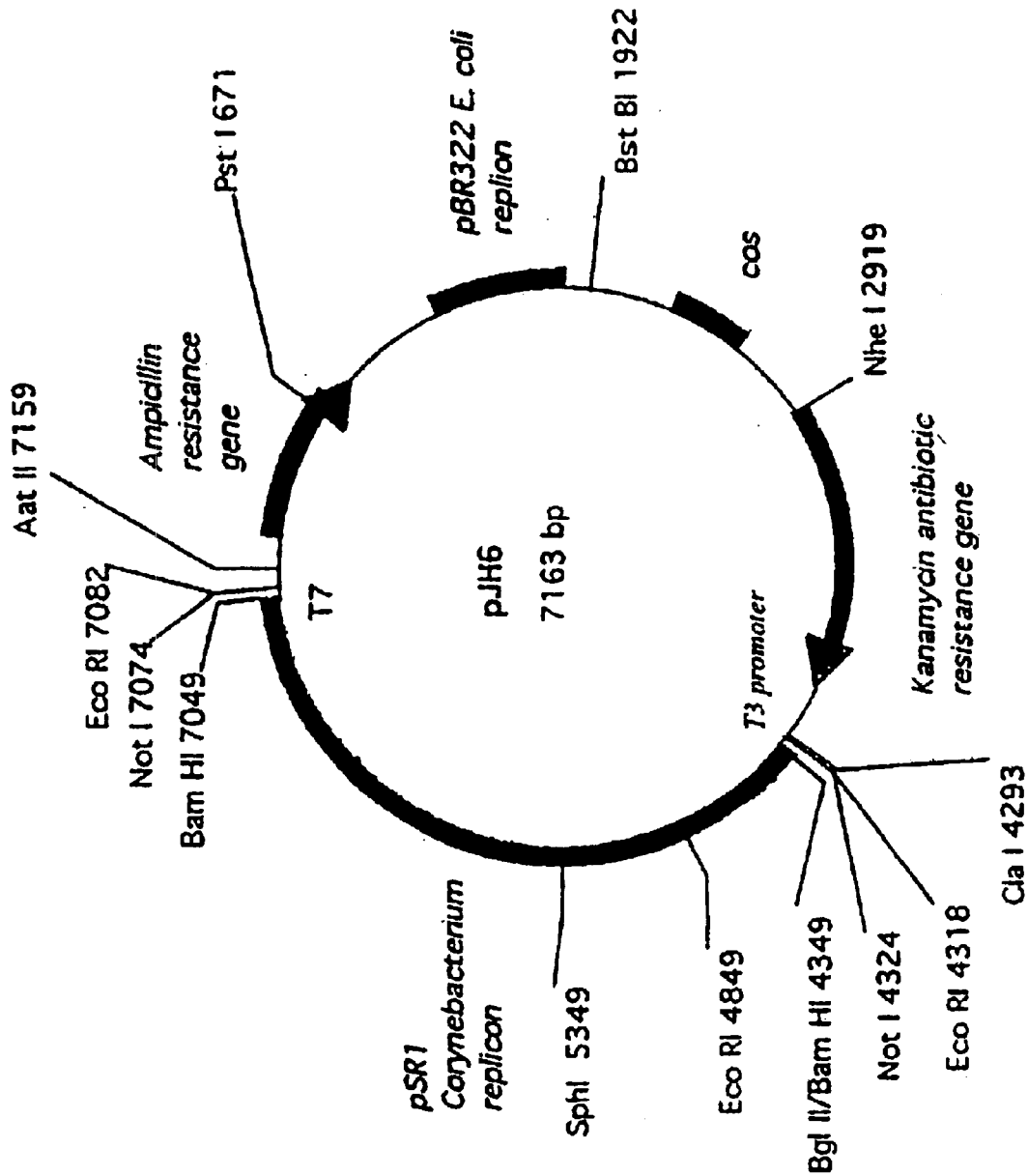

FIG. 8—shows a schematic diagram of the PJH6 vector of the present invention, as described in the Examples below. This encodes the pSR1 replicon (supra) and the pBR322 replicon for replication in E. coli. Antiobiotic resistance markers are ampicillin (E. coli) and kanamycin (E. coli and mycolic acid bacteria). Transcription across the insert can be provided by exogenous expression of the T7 RNA polymerase (in vitro or in vivo).

EXAMPLES

Example 1

A Novel Medium for Oligotrophic Screening

"MMRN" is prepared as a multicomponent stock to avoid the production of uncharacterised compounds during autoclaving. A "basic salts" stock is prepared containing 6 g/L $Na_2HPO_4$; 3 g/L $KH_2PO_4$; 1 g/L NaCl; 4 g/L $(NH_4)_2SO_4$; adjusted to pH 7.4 and made up to 989 mls with distilled water and autoclaved. A "100×A salts" solution is prepared consisting of 20 g/L $MgSO_4$; 2000 mg/L $FeSO_4 \cdot 7H_2O$; 200 mg/L $FeCl_3$; 200 mg/L $MnSO_4 \cdot H_2O$ is prepared in distilled water and autoclaved. A "1000×B salts" solution consisting of 500 mg/L $ZnSO_4 \cdot 7H_2O$; 200 mg/L $CuCl_2 \cdot 2H_2O$; 200 mg/L $Na_2B_4O_7 \cdot 10H_2O$; 100 mg/L $(NH_4)_7Mo_6O_{24} \cdot 4H_2O$ is prepared in distilled water and autoclaved. To prepare 1 litre of MMRN, sterile solutions of 989 mls basic salts, 10 mls 100×A salts, 1 ml 1000×B salts are combined. For solid media, agar is added to 1.4% w/v. Carbon-energy sources are supplemented to 80 μM final concentrations for soluble molecules, or as vapour for insoluble molecules (where their concentration is decided by their individual partition coefficients generally ranging from 3 to 40 μM). Petri plates or liquid cultures are incubated at 28° C. to 30° C. for up to 72 hours to accumulate sufficient biomass for genetic and biochemical testing.

Example 2

Isolation of Novel Strains of Mycolic Acid Containing Bacteria from Environmental Samples Using an Oligotrophic Screen and MMRN Novel strains are a source of genetic diversity from which biosensors specific for particular xenobiotic compounds can be constructed. To isolate mycolic acid bacteria, for example Rhodococcus/Nocardia, from an environmental matrix such as soil, a rapid isolation technique is required. Isolation of bacteria from soil using standard laboratory media containing eutrophic levels of carbon preselects for eutrophic bacteria which can grow rapidly under these conditions. Oligotrophic bacteria such as Rhodococcus/Nocardia are rarely successfully isolated on such rich media. This can be carried out using MMRN to specifically enrich for and subsequently purify strains of mycolic acid-containing bacteria which encode catabolic pathways whose expression is induced by a given xenobiotic. This methodology identifies molecules which are not only substrates, but are necessary and sufficient to induce the appropriate catabolic pathway. Soil suspensions from a matrix likely to express a desired phenotype (for instance a site known or believed to have been contaminated with a particular xenobiotic) can be used to inoculate MMRN supplemented with an oligotrophic level of a easily utilised carbon source (50 $\mu$M). This provides an initial oligotrophic screen. Oligotrophic mycolic acid-containing bacteria are slow growing and may be expected to have formed colonies after 72 hours incubation at 28° C. on MMRN paraffin. The incubation temperature appears to be highly selective of soil Nocardioform bacteria; Petri plates incubated at temperatures above 30° C. fail to show detectable colonies. Colonies growing on alkanes can be initially screened for Nocardioform phenotype, selecting for crumbling, crenellated colonies, (possibly mucoid on rich media). Gram- and Ziehl-Neelsen-staining tests rapidly identify Gram-positive, mycolic acid-containing bacteria (Place a slide carrying a heat fixed film on a slide carrier over a sink. Flood with carbol fuchsin solution (basic fuchsin 5 g; phenol, crystalline, 25 g; 95% or absolute ethanol 50 ml; distilled water 500 ml) and heat until steam rises. Leave for 5 minutes, heating occasionally to keep the stain steaming. Wash with distilled water. Flood slide with 20% v/v sulphuric acid; wash off with distilled water, and repeat several times until the film is a faint pink. Finally wash with water. Treat with 95% v/v ethanol for 2 minutes. Wash with distilled water. Counterstain with 0.2% w/v malachite green. Wash and blot dry. Acid and alcohol fast organisms are red, other organisms are green).

Mycolic acid-containing bacteria may then be screened for specific hydrocarbon-inducible catabolic pathways using MMRN supplemented with the target xenobiotic pollutant. Strains for which the target molecule is growth inducing may then be isolated and used to as a source of genetic regulatory elements for biosensors or as specific biocatalytic functions. Using this protocol mycolic acid containing bacteria have been and may be rapidly identified with novel and useful catabolic properties. This approach is also useful for identification and isolation of mycolic acid containing bacteria with biocatalytic properties.

Example 3

Method for Isolation of Total DNA from Mycolic Acid Bacteria

Bacterial strains were inoculated into 10 mls of MMRN supplemented with 5000 $\mu$M glucose 2% w/v L-glycine and incubated at 28° C. for 30 to 40 hours. This medium supports relatively rapid growth of mycolic acid bacteria cells. The L-glycine present is misincorporated into peptidoglycan cell wall substantially weakening its resistance to osmotic shock (Katsumata, et al., 1984). Growth on MMRN appears to enhance the uptake of L-glycine and its apparent misincorporation into the cell arabinogalactan. During this growth phase, mycolic acid bacteria produce extensive surfactants which cause the accumulated biomass to clump into pellicles and exhibit a strong surface tension effect. These pellicles, which are highly resistant to lysozyme, may be broken up and the concentration of biosurfactants substantially reduced by washing the cell pellet in several culture volumes of 10 mM Tris pH8.0; 0.1 k Tween 80 and finally resuspended in 1 ml of 10 mM Tris HCl pH8.0, containing 10 mg/ml lysozyme. The lysozyme reaction is incubated 60 to 100 minutes at 37° C. depending on the strain involved. Lysis is achieved by addition of 2% final (w/v) sodium dodecyl sulphate at 60° C. 40 minutes. The nucleic acids are selectively purified from the cellular debris by sequential phenol, phenol:chloroform:isoamyl alcohol (50:48:2 v/v) extractions. Nucleic acids are concentrated by ethanol precipitation in 2 M ammonium acetate. The nucleic acid pellet recovered is washed with 70% ethanol and resuspended in 100 $\mu$l 10 mM Tris.HCl pH8.0, 1 mM EDTA. 2 $\mu$l of this sample may be digested using restriction enzymes.

Example 4

Method to Isolate Supercoiled/circular Plasmid DNA from Mycolic Acid Bacteria 50 mls' *Rhodococcus* was cultured to mid-logarithmic phase in MMRN supplemented with 2% w/v L-glycine, 2% w/v D-glucose.

The cell pellet was washed in 10 mM Tris pH8.0 and 0.1% Tween 80. Resuspend cell pellet in 7.6 ml 6.7% sucrose; 50 mM Tris.HCl; 1 mM EDTA. Add 2 ml 40 mg/ml lysozyme in 10 mM Tris.HCl 1 mM EDTA. Incubate 37° C. 15 minutes. Add 970 $\mu$l 250 mM EDTA, 50 mM Tris.HCl pH 8.0. Continue incubation for a further 105 minutes 37° C. Lyse cells by addition of 600 $\mu$l 20% SDS 50 mM Tris.HCl, 20 mM EDTA pH 8.0. Incubate 55° C. 30 minutes. Shear lysate by vigorous vortexing 30 seconds. Denature DNA by addition of 560 $\mu$l freshly prepared 3 M NaOH followed by gently mixing 10 minutes room temperature. Neutralise by addition of 1 ml 2.0 M Tris.HCl pH 7.0 with gentle mixing 10 minutes. Add 2.1 ml 20% SDS 50 mM Tris.HCl, 1 mM EDTA. Mix gently. Add 4.2 ml ice cold 5 M NaCl. Incubate on ice overnight or for several hours at least. Clear the cellular debris by centrifugation at 48000 g 4° C. 90 minutes. The supernatant contains the DNA. Decant the supernatant by addition of an equal volume of ice cold isopropanol. Incubate −20° C. 30 minutes. Pellet nucleic acids 4° C., 10000 g 20 minutes.

Example 5

Novel Plasmids and Replicons Obtained by the Method of Example 4

Two multicopy plasmid replicons were isolated using the method of Example 4; pRC158 from strain RC158 and pRC100 from *R. corallina*.

Both plasmids have been digested with restriction enzymes to produce characteristic restriction patterns (FIGS. 1 and 2).

Plasmid pRC100, an approximately 100 kb supercoiled circular plasmid present in *R. corallina* was prepared as described in the text. The agarose gel was loaded in lane 1 with Lambda DNA HindIII size markers (23,130 bp; 9,416 bp, 6,557 bp, 4,361 bp, 2,322 bp, 2,027 bp, 564 bp); lanes 2 to 9 inclusive were loaded with pRC100 digested with BamHI (5'GGATCC3'), BclI (5'TGATCA3'), BgIII (5'AGATCT3'), EcORI (5'GAATTC3'), HindIII (5'AAGCTT3'), KpnI 5'(GGTACC3'), SacI (5'GAGCTC3'), SalI (5'GTCGAC3') restriction endonuclease reactions which were carried out under standard conditions; lane 10 contains undigested (presumable supercoiled) pRC100 DNA; lane 11 pWW110/40121, lane 12 pWW110/4011; lane 13 pWW15/3202; lane 14 pUC18 lane 15 blank. The DNA fragments have been resolved on a 0.8% Agarose Tris-Acetate-EDTA gel. Southern blotting analysis using Gram-negative mono and polyaromatic catechol 2,3-dioxygenases failed to detect significant sequence conservation.

Plasmid pRC158 is a supercoiled plasmid of approximately 14.57 kb. The plasmid was digested with the EcORI (5'GAATTC3') restriction endonuclease under standard conditions. The DNA fragments have been resolved on a 0.8% Agarose Tris-Acetate-EDTA gel. This pattern is unique and characteristic to pRC158. The plasmid contains at least five EcORI restriction enzyme sites which can be used to digest the plasmid into a specific restriction pattern of five major restriction fragments of 4.3, 3.3, 2.9, 2.2 and 1.6 Kb DNA respectively.

These plasmids are relatively small, exhibit a high plasmid copy number and are easily isolated from *Rhodococcus/Nocardia*. Therefore, they possess several characteristics which are suitable for the construction of *Rhodococcus/Nocardia* cloning vectors.

The DNA sequence of the minimal replicon regions of these plasmids may be determined by screening fragments obtained therefrom in disabled vectors containing marker proteins (for instance based on pJP7 described below) to see if they can replicate in mycolic acid bacteria.

Further plasmids e.g. pCY101 have also been isolated and sequenced using the methods of the present invention. The replicon from this plasmid was used in pJP8.

EXAMPLE 6

Hybridisation Screening for Novel Promoters and/or Operon Proteins

The test sample (host cells) are contacted with a nucleic acid molecule probe (preferably around 100 nucleotides or more) based on FIGS. 4A–4L under suitable hybridisation conditions, and any test DNA which hybridises thereto is identified. Such screening is initially carried out under low-stringency conditions, which comprise a temperature of about 37° C. or less, a formamide concentration of less than about 50%, and a moderate to low salt (e.g. Standard Saline Citrate ('SSC')=0.15 M sodium chloride; 0.15 M sodium citrate; pH 7) concentration. Alternatively, a temperature of about 50° C. or less and a high salt (e.g. 'SSPE'=0.180 mM sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of similarity with the probe sequence, without requiring the perfect homology for the identification of a stable hybrid. The phrase 'substantial similarity' refers to sequences which share at least 50% overall sequence identity. Preferably, hybridisation conditions will be selected which allow the identification of sequences having at least 70% sequence identity with the probe, while discriminating against sequences which have a lower level of sequence identity with respect to the probe. After low stringency hybridisation has been used to identify several clones having a substantial degree of similarity with the probe sequence, this subset of clones is then subjected to high stringency hybridisation, so as to identify those clones having a particularly high level of homology with respect to the probe sequences. High stringency conditions comprise a temperature of about 42° C. or less, a form amide concentration of less than about 20%, and a low salt (SSC) concentration. Alternatively they may comprise a temperature of about 65° C. or less, and a low salt (SSPE) concentration. Preferred conditions for such screening comprise a temperature of about 42° C., a formamide concentration of about 20%, and a salt concentration of about 2×SSC, or a temperature of about 65° C., and a salt concentration of about 0.2 SSPE.

Example 7

Cloning Aromatic Degradative Operon from *Rhodococcus corallina* by Functional Screening in *E coli*

To demonstrate the potential mycolic acid bacteria (e.g. *Rhodococcus/Nocardia*) have as biosensors and biocatalysts as well as to validate the novel genetic tools and approach to cloning of the present invention, a gene cluster or operon associated with aromatic degradation was cloned and isolated from *Rhodococcus corallina*. This gene cluster/operon appears to be a broad substrate range monoaromatic degradative pathway and has been designated monoaromatic catabolic (mac) gene cluster or operon. *R. corallina* was isolated from pristine soil in Canada and is an acknowledged *Rhodococcus* type strain. This strain encodes a broad range of catabolic activities which include toluene, benzoate, phenol, cumine, cyamine. Genetic induction of the toluene degradative pathway in *R. corallina* occurs when toluene is supplied as vapour. This is a level of less than 200 ppm in water. Therefore, the sensitivity inherent in the biology of *Rhodococcus* is very close to those levels expected for biosensors in industrial use. Similar experiments using a naphthalene utilising *Rhodococcus* which is also supplied as a vapour Biochemical assays of ring cleavage dioxygenase activities in crude enzyme extracts of *R. corallina* cells grown on MMRN supplemented with different growth-inducing xenobiotics indicated that the molecular specificity of ring cleavage dioxygenase induction is good. Toluene induced the meta pathway (although some ortho activity was observed) whereas benzoate and phenol exclusively induces the ortho pathway. Xylene, which is very closely related to toluene does not act as a growth inducing substrate. The closely related compounds toluene and benzoate but not xylene induce different ring-cleavage enzymes despite their relatively similar molecular shape. This behaviour and absence of induction with xylene suggests that the receptor for these or metabolites derived from these molecules is sensitive to minor electrostatic changes in their ligand. This strongly asserts that genetically constructed biosensors derived from these receptor molecules and their regulated promoter(s) will exhibit a level of specificity which exceeds that currently available as field test systems.

Since a clear catechol 2,3-dioxygenase activity was induced by toluene, but not by benzoate (indicating that the meta pathway in this strain is specifically induced by toluene), the catechol 2,3-dioxygenase activity can be used as a marker for gene(s), gene cluster(s) or operon(s) involved in its degradation.

The *R. corallina* catechol 2,3-dioxygenase structural gene was isolated by functional screening of a partial Sau3A restriction enzyme digest-generated gene library in *E. coli* hsdRMmcrAB for using the commercially available cosmid cloning vector pWE15 (Wahl et al., 1987).

Because only a single enzyme activity has been used as a functional marker rather than complete acquisition of a phenotype and given the diversity of *Rhodococcus/Nocardia* metabolism and the genetic incompatibility between mycolic acid bacteria and *E. coli* it is possible that numerous catechol dioxygenases may exist but only some will be expressed successfully in *E. coli*. To facilitate expression of cloned DNA irrespective of the presence of an indigenous promoter element, a phage T7 promoter is located adjacent to the pWE15 unique BamHI restriction site into which the rhodococcal DNA was inserted. Phage T7 RNA polymerase (a single polypeptide) is supplied in trans from pGP1-2Sm.

As a functional screen for 2,3-dioxygenase activity, catechol was sprayed onto nutrient agar plates supplemented with 15 µg/ml kanamycin, 50 µg/ml streptomycin, 0.1 mM isopropyl thiogalactoside (IPTG) incubated at 30° C. to accumulate biomass. The expression of T7 polymerase is repressed by temperature sensitive phage lambda repressor which is itself expressed from an IPTG induced lacUV5 promoter. Thus incubation at 42° C. leads to induction of T7 polymerase expression and so transcription of the pWE15 insert region from the T7 promoter (i.e. one direction of transcript alone).

Using the pGP1-2Sm T7 expression system, two colonies were isolated which encoded the characteristics catechol 2,3-dioxygenase activity from *R. corallina*. From approximately 3000 colonies of individual primary clones of *R. corallina* gene library in an *E. coli* hsdRMmcrAB strain, two colonies were observed to produce a deep yellow colour indicative of catechol 2,3-dioxygenase activity (2-hydroxymuconic semialdehyde) when exogenous catechol was supplied in phosphate buffer (0.1M pH7.4). These clones were designated clone #1 and clone #2. Restriction enzyme mapping of both clone #1 and clone #2 DNA showed that both encode overlapping regions of DNA but were otherwise nonsibling clones; this is compatible with a primary screening of a cosmid library.

Southern blot analysis of *R. corallina* total cellular and plasmid DNA confirmed that the isolated catechol 2,3-dioxygenase locus in clones #1 and #2 are contiguous with an approximately 35 kb region *R. corallina* genomic DNA. The common region to both clones is comprised of seven major EcORI restriction fragments (8.3, 7.2, 5.2, 4.9, 4.3, 2.4, 2.3 Kb respectively 34.6 kb in total). To confirm the continuity and source of the clone #1 and clone#2 inserts, an aliquot of clone #2 DNA, which contained a slightly longer *R. corallina* DNA insert than clone #1, was used as a source of DNA to synthesise a radioactive probe to identify homologous DNA restriction fragments present in an EcORI restriction digest of total cellular *R. corallina* DNA as well as other bacterial DNA samples. An randomly picked pWE15 clone which did not express catechol 2,3-dioxygenase was chosen as one control (cosmid clone "clone # 4") and *E. coli* genomic DNA were selected as control DNAs. At the level of accuracy of the gel, the coincidence of the catechol 2,3-dioxygenase clones #1 and clone #2 DNA inserts relative to the genomic *R. corallina* EcORI and SmaI restriction maps indicated that no gross deletions or rearrangements had occurred during the cloning. Significantly, there was no evidence for a supercoiled plasmid location for the catechol 2,3-dioxygenase gene indicating that the locus is chromosomally encoded (although pRC100 has been isolated from *R. corallina* (see FIG. 1) this strain does not encode large linear plasmids). To investigate the potential for gene homologs to be identified a *Rhodococcus* strain RC161 which was isolated from North East England and so is distinct from *R. corallina* (which also degrades toluene via meta cleavage but was isolated form soil in Canada) was included in the Southern Blot. There were three RC161 EcORI restriction fragments which exhibited significant DNA sequence conservation with *R. corallina* sequences in clone #2. The nature of these sequences is under investigation.

Colony hybridisation to the *R. corallina* gene library secondary screen using the 2.4 Kb EcORI restriction fragment of clone #2 as a source of radioactive probe identified four cosmid clones, pWE15#C, pWE15#D, pWE15#B and pWE15#G encoding overlapping regions of the *R. corallina* chromosome. Thus a region of the *R. corallina* genome with a contiguous length of approximately 70 kb has been cloned and isolated. These cosmids will provide a source of *R. corallina* DNA for future experiments.

The 35 Kb region encoded by clones #1 and #2 was mapped using four six base recognition restriction enzymes. An analysis of the map does not indicate inverted DNA map elements which could be consistent with a transposable element. This does not, however, preclude this possibility existing.

The sequence of the operon is described in Example 9 below.

Further plasmids which may be used for screening in accordance with the methods of the present invention are as follows:

pRV1

This is shown in FIG. 7. It encodes the pSR1 replicon for *Corynebacterium*, the pUC replicon for *E. coli*, the RP4 oriT and a minimal cos PCR product. The multiple cloning site is under the control of the lac operon promoter allowing expression in *E. coli*.

The cos sequence in currently available in cosmids such as pWE15 (Stratagene) and is encoded within an approximately 1 Kb region. However experiments showed that cos induced structural instability in several different plasmids. Analysis of the cos region in lambda suggested that the instability may be due to high levels of transcription entering the plasmid cos site and or transcription through adjacent lambda coding sequences which flank cos in the standard cosmid cloning vectors. To avoid problems with these extraneous elements, using computer-aided sequence analysis, the present inventors designed oligonucleotide primers to amplify the minimal cos element, free from flanking genes which may induce instability and occupy valuable cloning space. Additionally, experiments indicated that the cos PCR product induced structural instability in vectors carrying it. Therefore the cos PCR product was cloned into pRV1 (a preferred shuttle vector of the present invention) into a transcriptional quiet region of the plasmid. Transcription was blocked using a transcriptional terminator (trpA terminator from *E. coli*). This construct combines cosmid function with a mycolic acid replicon, an *E. coli* replicon, a selectable marker, a conjugative oriT, and a unique BamHI cloning site.

Briefly, the plasmid was prepared by cleaving plasmid pWSTIB (Peoples et al, 1988 Mol Microbiol 2(1): 63–72) with NheI and SalI to clone the *C glutamicum* replicon into the mobilisable plasmid pK19mob (Shäfer et al, 1994 Gene 145: 69–73) to form a shuttle vector designated pJH4. The minimal Cos site from wild-type phage (Promega) was amplified by PCR using primers which introduced two XbaI sites (5' TCTAGA 3') into the fragment.

The primers were:

F: 127 5'CGCTGATTTGTATTGTCTG 3'145 (SEQ ID No. 9)

R: 502 5'GACTTCCATTGTTCATTCC 3'484 (SEQ ID NO. 10)

F: 51171 5'AAAAGACGTCGGTGCTAATAAGGGA-CAGTG 3'51190 (SEQ ID NO. 11)

R: 51395 5'AAAAGACGTCACAAAACAGCAGGGAAG-CAG 3'51376 (SEQ ID NO. 12)

The fragment was cloned into pJH4 to give pRV1.

pJH6

This is shown in FIG. 8. It also encodes the pSR1 replicon for *Corynebacterium*, the pUC replicon for *E. coli*, the RP4 oriT and a minimal cos PCR product. Inserted genes are expressed under the T3 and T7 promoters which are controlled by temperature shift, allowing the controlled production of genes which may impose a lethal phenotype.

Briefly, the plasmid was prepared by cleaving plasmid pWE15 (stratagene) with Agl III enzyme to remove unwanted SV40 ori and Neo sties. The NheI/BstBI fragment of pK18mob (Shäfer et al, 1994 Gene 145: 69–73) was cloned into pWE15-small to add a kanamycin resistance marker known to work in *C glutamicum* and *E coli*. The plasmid pWSTI B (above) was cleaved with BglII and BamHI enzymes to clone the pSR1 origin of replication of *C glutamicum* into pWE1S-small. Finally RP4(OriT) was amplified by PCR using the following primers, which incorporate AatII restriction site:

F: 51171 5' AAAAGACGTCGGTGCGAATAAGGGA-CAGTG 3' 51190

R: 51395 5' AAAAGACGTCACAAAACAGCAGG-GAAGCAG 3' 51376

The amplified fragment was cloned into the AatII site of the pWE15-small-Km-pSR1 construct to form the shuttled vector designated pJH6.

Example 8

A Method for Gene Isolation from Mycolic Acid-containing Bacteria by Functional Screening in *Corynebacterium glutamicum*

A key aspect of this invention is the ability to genetically manipulate a variety of strains or species of mycolic acid-containing bacteria such as *Rhodococcus/Nocardia* in a simple, effective way so as to clone and isolate gene(s), gene cluster(s) or operon(s) with applications as biosensors or biocatalysis.

The closely related mycolic acid-containing bacterium *Corynebacterium glutamicum* may be used as a host to express *Rhodococcus/Nocardia* genetic material. *C. glutamicum* shares a common cell wall type and probably similar genetic regulation to *Rhodococcus/Nocardia* but since it has been used extensively for the industrial production of amino acids and nucleotides it has lost or may never had encoded significant xenobiotic catabolic activity. It therefore represents a good "naive" host to express *Rhodococcus/Nocardia* genes.

Restriction enzyme activity in natural isolates of *Rhodococcus/Nocardia* effectively limits the efficiency of electroporation to very low, or undetectable levels. Most restriction enzymes recognise double stranded DNA exclusively. Because single-stranded DNA is a necessary product of a replication fork, normal restriction enzyme activity in bacterial cells is limited to double stranded DNA substrates. Conjugative DNA transfer in Gram-negative, and most probably between Gram-positive bacteria as well, involves a single-stranded DNA intermediate. Conjugative DNA transfer should thus, generally, be relatively immune to restriction.

pJP8

The pJP8 plasmid may be used to introduce the library in the first host into a suitable mycolic acid bacterium such as *corynebacterium* or any mycolic acid bacterium which does not encode the desired phenotype.

The pJP8 plasmid is shown in FIG. 5. The shuttle vector carries a approximately 400 bp region of the IncP RK2 conjugative plasmid which encodes the origin of transfer. This may be complemented in trans by IncP tra functions maintained on a suitable compatible recombinant plasmid, or as an integrated construct in the host chromosome or by RK2 itself (modified to disrupt its kanamycin resistance gene—a marker used for pJP8)

Conjugation involves "effective contact" between the donor and recipient cells, which in this case are *E coli* encoding complementing tra functions and bearing the mobilizable cosmid vector and a suitable mycolic acid bacterium respectively. Effective contact is the formation of a cytoplasmic bridge between the two cells through which conjugative DNA transfer occurs. Thus donor and recipient cells are grown to mid to late logarithmic phase of growth in Lauria Bertini broth and MMRN supplemented with suitable carbon source at 37° C. and 30° C. respectively. Donor and recipient cells are washed in prewarmed media and mixed on a solid support matrix such as Lauria Bertini Agar plate and incubated at 37° C. for up to 16 hours. The mating mixture is scraped from the plate and resuspended in 30° C. Lauria Bertini broth, from which serial dilutions are prepared and plated on MMRN agar supplemented with drugs to counter select against the donor and recipient and select for the transconjugant mycolic acid bacterium. Commonly, naladixic acid selects against the donor and kanamycin resistance selects against the recipient. Thus, on a plates supplemented with both only the transconjugant may grow. The plates are incubated at 30° C. for 40 hours.

Example 9

DNA Sequence of the Proximal Region of *R. corallina* ohp Locus

The DNA sequence of approximately 7 Kb of *R. corallina* chromosomal DNA surrounding a catechol 2,3-dioxygenase has been determined using automated dye terminator sequencing reactions. A schematic of the current state of the data is presented in FIG. 3 which shows at least seven genes which have been identified by protein sequence conservation with known protein motif data (nitropropane dioxygenase, a putative regulatory protein orfR, monoaromatic monooxygenase, hydroxymuconic semialdehyde hydrolase, catechol 2,3-dioxygenase, alcohol dehydrogenase).

The sequence of this region in shown in FIG. 4.

The predicated gene organisation of the ohp associated region is indicative of the presence of possibly two different catabolic gene clusters or operons; one involving the nitropropane dioxygenase the other the ohp gene cluster or operon. Such a genetic organisation suggests that a set of divergent promoter elements are located between the predicted regulatory gene orfR and the ohp monooxygenase structural gene. Similarly, another promoter could map immediately upstream of the divergent open reading frame which has conservation to nitropropane dioxygenase.

Example 10

Use of the Promoter Obtained in Example 9

The *R. corallina* genes identified by sequence conservation or by function are listed in FIG. 3. These are potentially useful as catalytic functions in various chemical transformations. The regulatory protein associated with the putative oho operon (possibly encoded by orfR) is involved in the control of transcriptional initiation at its target promoter. This regulatory protein encodes the specificity of the operon and as such is likely to be central to the biosensor function. Subcloning of the regulatory protein and its target promoter could permit novel biosensor activities to be introduced into other *Rhodococcus/Nocardia* strains. In addition, if this regulatory protein is subjected to mutagenesis, mutants with altered function could be identified (using a luciferase promoter probe driven by the regulated promoter). The regulatory protein has a specific capability to bind its ligand from the environment. It is therefore potentially useful as a protein adsorbent for specific molecules. This could have application in analytical chemistry sample preparation.

An analysis of the 5' region of the predicted genes and the catechol 2,3-dioxygenase reading frame has allowed us to predict the sequence involved in translational initiation. These "ribosome binding sites" can be used as sequence guides or templates for the creation of synthetic oligonucleotides encoding functional *Rhodococcus/Nocardia* translational initiation sites. Mutagenesis of this region can identify potentially up and down regulating base sequences changes.

The ohp promoter region which controls expression of the cloned operon lies between two putative genes (orfR regulatory gene and orfT transport gene). In addition to forming the basis of a biosensor, the promoter and its cognate regulatory system also could be used as an inducible expression system for *Rhodococcus/Nocardia* and other mycolic acid-containing bacteria. The sequence of this region encodes the binding sites and regulatory elements or operators involved in control of the ohp and possibly other closely linked genes or operons. This region constitutes the first defined sequence for a *Rhodococcus/Nocardia* promoter region. It can be used as a probe to identify similar sequences within other mycolic acid containing bacteria such as *Rhodococcus/Nocardia*. This promoter sequence could be used as a region of homology to drive targeted recombination/insertion of signal gene(s) such as *Vibrio* luciferase.

A vector such as pJP7 (FIG. 6) may be used as follows:

The vector is a 'suicide vector' which can be used to drive expression of bacterial luciferase genes in *R. corallina*. A portion of the ohp promoter region (FIG. 4) is ligated into the unique pJP7 XbaI restriction site downstream of an *E. coli* trpA transcriptional terminator. The sacB gene allows counter selection for the integrated plasmid thus selecting for a second cross-over within the plasmid sequences to produce a gene replacement of the wild type gene with an interrupted gene including luciferase. An aspect to this technique is the ability to introduce DNA constructs into the target cell in a hyperrecombinogenic, non-replicating form. Conjugatively mobilised plasmids may represent just such a form in that they may be single-stranded form. Thus the conjugatively mobilised plasmid pJP7 which cannot replicate in mycolic acid bacteria could be used directly to integrate DNA constructs into a wide range of mycolic acid bacterial strains.

Example 11

Biosensor

The biosensor of the present invention is typically a recombinant mycolic acid containing bacteria which may be *Rhodococcus/Nocardia* cell. The natural gene-regulatory system which activates expression of catabolic gene(s), gene cluster(s) or operon(s) in response to the presence of specific class or type of inducing naturally-occurring or xenobiotic carbon substrate(s) has been genetically manipulated to induce the expression of some signal gene(s), such as (but not limited to) the *Vibrio* or *Photobacterium* bacterial luciferase in the presence of the inducer. This manipulation may have involved either incorporation of the signal gene(s) into a chromosomally- or episomally-encoded regulon under the control of a suitable environmentally-regulated promoter, or by direct sub-cloning of the regulated promoter to a rhodococcal/nocardial plasmid or other replicon or episomal element encoding a promoter-less signal gene(s). The genetic manipulation effecting the substitution or supplementation of the natural genes with the signal gene(s) may involve integration of the signal gene(s) gene cluster(s) or operon into the host chromosome, plasmid or other episomal element so as to place it under inducible regulatory control or subcloning of the analyte (particularly hydrocarbon)-responsive promoter to a multicopy plasmid. The integration may involve site-specific recombination, transposition or illegitimate or homology-driven DNA recombination which is another aspect of this invention; however other methods of DNA integration such as the use of polymerase chain reaction (PCR) are not ruled out.

Signal to noise ratio can be readily improved in the recombinant system by enhancing or optimising expression or function of the signal gene, which may be luciferase, by means of improved gene translational signals and/or increasing levels of transcription by either raising transcriptional rates, mRNA stability or gene dosage of the construct (by subcloning to a plasmid or iterative gene integrations into a chromosome, plasmid or other episomal element). Thus, for instance, transcriptional efficiency of the luciferase genes luxAB can be increased by substitution of the *Vibrio* translational initiation signals with those from the ohp operon.

REFERENCES von der Osten et al (1989) Biotechnol Letts 11: 11–16.
Wahl et al (1987) Proc Natl Acad Sci 84: 2160–2164.
Katsumata et al (1989) J Bacteriol 159: 306–311.

What is claimed is:

1. An isolated nucleic acid molecule comprising a nucleotide sequence encoding an operon protein, which operon protein is the Regulator (REG) protein of the *R. corallina* ohp operon.

2. A nucleic acid molecule as claimed in claim 1 wherein the nucleotide sequence encodes an amino acid molecule having the sequence of SEQ ID NO: 3.

3. A nucleic acid molecule as claimed in claim 2 wherein the nucleotide sequence is from nucleotides 295 to 1035 of SEQ ID NO: 1.

4. A nucleic acid molecule as claimed in claim 1 further comprising an inducible promoter region of the nucleotide sequence SEQ ID No: 1 encoding the *R. corallina* ohp operon having the genes shown in FIG. 3 wherein the Regulator (REG) protein controls transcriptional initiation of said inducible promoter region.

5. A nucleic acid molecule as claimed in claim 4 wherein the inducible promoter region is the ohp promoter region which lies between nucleotides 1035 and 1450 of SEQ ID NO: 1.

6. A nucleic acid molecule as claimed in claim 4 further comprising a heterologous reporter gene operably linked to the inducible promoter region.

7. A vector comprising the nucleic acid molecule of claim 6.

8. A vector as claimed in claim 7 comprising at least one of the following: luxAB reporter genes; sacB gene; antibiotic resistance; RP4/RK2 mobilizing elements.

9. A vector as claimed in claim 8 comprising lux AB reporter genes, sacB gene, kanamycin and thiostrepton resistance genes, an *E. coli* origin of replication, and RP4 mobilizing elements.

10. A method of transforming a host cell comprising introducing the vector of claim 7 into a host cell.

11. A method as claimed in claim 10 wherein the host cell is a mycolic acid bacterium of the same strain from which at least one of the inducible promoter and operon proteins were isolated.

12. An isolated host cell transformed with the vector of claim 7.

13. A vector comprising the nucleic acid molecule of claim 1.

14. A vector as claimed in claim 13 comprising one or more of the following: luxAB reporter genes; sacB gene; antibiotic resistance; RP4/RK2 mobilizing elements.

15. An isolated host cell transformed with the vector of claim 13.

16. A method of introducing an operon protein into a host cell, which operon protein is the regulator (REG) protein of the *R. corallina* ohp operon, said method comprising the step of transforming said host cell with a vector as claimed in claim 13.

* * * * *

SEQUENCE LISTING

<160> NUMBER OF SEQ ID NOS: 12

<210> SEQ ID NO 1
<211> LENGTH: 7584
<212> TYPE: DNA
<213> ORGANISM: Rhodococcus corallina

<400> SEQUENCE: 1

```
gaattccatg ttcttctcct tgcatgtggc ccgcgttgcc gagggcactg ctcggcctgt      60
cgcccgcaga gggcgcatgt ccgggtgcct ggatatggcg cgtacggcgt gccctccggc     120
gttaaccccg aggttggcca cgatgcccg gccatcaggt ctggaatgct agcgttccag     180
acgaaggtaa cccacagtga ctcacaccac aagtactaga atgcaagctg ttgcggtgag     240
cgccgcggca taagggggag ccatgtccgg gacgccgacg gaaagcctga ctcgatgacc     300
```

-continued

```
accaccgaca ccggccccaa gccgggcagt gaggccgccg ccctgctcgc caatgtccgc      360
acctcggggg cgcggctgtc ctccgcgttg tacgacattc tgaagaaccg gctgctcgaa      420
gggcgctatg cggcaggcga gaagatcgtc gtcgagtcga tccggcaaga gttcggggtg      480
agcaagcagc ccgtcatgga cgctctgcgc cgcctgtcca gcgacaagct ggtccacatc      540
gttccccagg tcggttgcga ggtcgtctcc tacgccccgc gcgaagtgga agacttctac      600
accctgttcg gcggtttcga agggaccatc gccgcggtag cggcctcccg gcggaccgag      660
gcccagttgc tggagctgga cctgatctcg gcgcgggtcg acgccctgat cacctcccac      720
gacccggtgg tccgcgcccg cgggtaccgc gtgcacaacc gggagttcca tgcggccatc      780
cacgcgatgg cgcactcgcg gatcatggag gagaccagcc agcgaatgtg ggatctgtcg      840
gacttcttga tcaacaccac cggcatcacc aacccgctct cgagcgcact gcccgaccgg      900
cagcatgacc accacgaaat caccgaggcc atccgcaacc gtgacgcagc tgccgcccgc      960
gaggccatgg aacgccacat cgtcggcacc atcgcagtaa tccgcgacga atccaacgcc     1020
cagctgccga gctagacccc gatacccggg ccatcgaccg gctccgctat cgcgccacct     1080
acgccgaggg gggactctcg gccgtagcgc tgcagacgat ccaccggcac cctccacgct     1140
gaccctgtc tcgccctaga gggcggcgc gccgtcgatc acctttaccc tcatccagag      1200
acttgcgtca ccctctatgc ccgagtagcg tctgaactag acgtctagca ttctagttga     1260
gtgctccctc tcgaagattc tccagagaac ccctctcgaa catccccaga agaaaggagc     1320
ggccatgacg accgcttcgc acgcatcgtc cttcggggca cgagcccact tccgcccaca     1380
gatcggggaa gcccgaccgt gagcaccaca cctacctccc cgacgaagac ctcaccgctg     1440
cgggtagcga tggccagctt catcggtacc accgtcgagt actacgactt cttcatctac     1500
ggcaccgcgg ccgcgctggt attccctgag ttgttcttcc cggatgtctc gtccgcgatc     1560
ggaatcctgt tgtcgttcgc gaccttcagc gtttgggttcc tcgcccgccc gctgggtggc     1620
atagtgttcg ggcacttcgg tgaccgggtc ggccgcaagc agatgctggt gatctccctg     1680
gtcggaatgg gctcggccac cgtactgatg ggattgttgc ccggttacgc ccaaatcggg     1740
atcgccgccc ccatcctgct gaccctgctg cgcctggtgc agggctttgc cgtcggcggc     1800
gagtggggtg gagccaccct gatggccgtc gagcacgccc ccaccgcgaa gaagggcttt     1860
ttcggatcct tctcccagat gggggcaccc gccgggacca gcgtcgcaac cctggcgttc     1920
ttcgcggtct cccaattgcc cgacgagcag ttcctgagtt ggggctggcg actgccgttc     1980
ctgttcagcg cggtgctgat cgtgatcggg ctgttcattc gcctgtccct ggccgaaagc     2040
cccgacttcg ccgaggtgaa ggcacagagc gccgtggtgc gaatgccgat cgccgaagcg     2100
ttccgcaagc actggaagga aattctcctc atcgcgggca cctacctgtc caaggagtg      2160
ttcgcctata tctgcatggc ctacctcgtc tcctacggca ccaccgtcgc ggggatcagc     2220
cgcaccttcg ccctggccgg agtattcgtc gccggcatcg tcgccgtcct cctctacctc     2280
gtgttcggcg ctctgtccga cactttcggc cgcaagacca tgtacctgct cggcgccgcc     2340
gcgatgggtg tggtgatcgc cccgccttc gcactgatca acaccggcaa cccgtggctg     2400
ttcatgccg cgcaggtgct ggtcttcgga attgcaatgg cccccgccgc cggcgtgaca     2460
ggctccctgt tcacgatggt cttcgacgcg gacgtgcgct acagcggtgt ctctatcggc     2520
tacaccatct cccaggtcgc cggctccgcg ttcgccccga cgatcgcgac cgccttgtac     2580
gcctccacca acaccagcaa ctcgatcgtg acctacctgc tgatcgtctc ggccatctcg     2640
```

-continued

```
atcgtctcgg tgatcctgct gcccggcggc tggggcgca agggcgctgc gagccagctc    2700
actcgcgacc aggccacctc cacaccgaaa atgcctgaca ccgaaacatt ttcgactcgg    2760
acagttccgg acaccgcagc atccctgcgc gtcctcgaca agtgaagtga tgacagacat    2820
gagtgaccac gaccgcacct cctacgacac cgacgtcgtg atcgtcggcc tcggccccgc    2880
cggtggcaca cgggcgcttg ccctggccag ctacggcatc cgcgttcacg ccgtctcgat    2940
gttcccctgg gtggcgaact cgccgcgcgc gcacatcacc aaccagcgcg ccgtcgaagt    3000
gctgcgtgac ctgggcgtcg aagacgaggc gcgcaactac gccaccccgt gggaccagat    3060
gggcgacacg ctgttcacca cgagcctggc cggcgaggga atcgtccgga tgcagacctg    3120
gggtacgggc gatatccgct acggggacta cctgtccgga agccctgca cgatgctcga    3180
cattccgcag cccctgatgg agccggtgct gatcaagaac gccgccgaac gtggtgcggt    3240
catcagcttc aacaccgaat acctcgacca cgcccaggac gaggacgggg tgaccgtccg    3300
gttccgcgac gtccgctcgg gcaccgtgtt cacccagcga gcccgcttcc tgctcggttt    3360
cgacggcgca cgatcgaaga tcgccgaaca gatcgggctt ccgttcgaag gtgaactcgc    3420
ccgcgccggt accgcgtaca tcctgttcaa cgcggacctg agcaaatatg tcgctcatcg    3480
gccgagcatc ttgcactgga tcgtcaactc gaaggccggt ttcggtgaga tcggcatggg    3540
tctgctgcgc gcgatccgac cgtgggacca gtggatcgcc ggctgggct tcgacatggc    3600
gaacggcgag ccggatgtct ccgacgacgt tgtcctcgaa cagatccgga ccctcgtcgg    3660
cgaccccgca ctgacgtcg agatcgtgtc gaggtccttc tggtacgtca accggcagtg    3720
ggctgagcac taccagtccg gtcgagtgtt ctgcggcggc gacgcggtgc accggcatcc    3780
gccgagcagc gggctgggct cgaacacgtc catgcaggac gcgttcaacc tggcatggaa    3840
gatcgcgttc gtcgtgaagg ggtatgcagg accgggtctg ctcgagtcct actctcctga    3900
gcgtgttccg gtcggcaaac agatcgtcgc tcgcgccaac cagtcccgca aggactacgc    3960
cgggctgcgc gaatggttcg atcacgagag cgacgacccg gtcgccgccg gcctggcaaa    4020
gttgaaggaa ccctcgtccg aaggtgttgc tctgcgtgag cggctgtacg aggcgctgga    4080
ggtgaagaac gccgaattca acgcccaggg cgtcgaactc aaccagcgct acacctcgtc    4140
cgcggtcgtt cccgacctcg aggcgggcga ggaagtgtgg gtgcgcgatc gtgagctgta    4200
cctgcaggcc accacccggc cgggcgcgaa gctgccgcat gcgtggctgg tcggcgccga    4260
cggaacccgc atctccaccc tcgacgtcac cggcaaggga atgatgaccc tgctgaccgg    4320
actcggcggc caggcatgga agcgtgccgc cgccaaactc gacctgccgt tcctgcggac    4380
cgtcgttgtc ggcgaacccg gcaccatcga cccttacgga tactggcggc gggtccgcga    4440
catcgacgag gccggcgccc tgctcgtgcg gcccgacggc tacgtcgcgt ggcgacacag    4500
tgctccggtc tgggacgaca ccgaagcgct caccagcctc gagaacgctc tcaccgcggt    4560
cctcgaccac tcgccagcg acaacgggaa cccgagcggc acaaacgagc gcagtacag    4620
cacccgggcc gtgccgatcg tcgttccgca cgttaccgcc gaggatgcag caccagcttc    4680
cgccacccgc accaccacag tcgagggaga gaaccgatga cccgtcctta caccagcgtc    4740
tgggacgacc tgaaccaggt cgagttcagc cagggattca tccaggccgg ccctaccgg    4800
acccgatacc tgcacgccgg cgattcgtcc aagcccacgc tgatcctgct gcacggcatc    4860
accggccacg ccgaggcgta cgtgcgcaat ctgcgctcgc attccgagca cttcaacgtc    4920
tgggcaatcg acttcatcgg ccacggctat tcgaccaagc ccgaccaccc gctcgagatc    4980
aagcactaca tcgaccacgt gctgcagttg ctggacgcca tcggcgtcga aaggcctcg    5040
```

-continued

```
ttttccgggg agtctctcgg cggttgggtc accgcccagt tcgcgcacga ccatcccgag    5100
aaggtcgacc ggatcgtgct caacaccatg ggcggcacca tggccaaccc tcaggtgatg    5160
gaacgtctct atacccgtc gatggaagcg gcgaaggacc cgagctggga acgcgtcaaa     5220
gcacgcctcg aatggctcat ggccgacccg accatggtca ccgacgacct gatccgcacc    5280
cgccaggcca tcttccagca gccggattgg ctcaaggcct cgagatgaa catggcactg     5340 caggacctcg aaacccgcaa gcggaacatg atcaccgacg ccactctcaa cggcatcacg    5400
gtgcccgcga tggtgctgtg gaccaccaag gaccccccg gtccggtcga cgaagccaag    5460
cgcatcgcct cccacatccc gggcgccaag ctggccatca tggagaactg tggccactgg    5520
ccccagtacg aggaccccga gaccttcaac aagctgcatc tggacttcct cctcggtcgc    5580
agctgacaca gaccccggcc ggtgccgcca acccctgcaa cccgggcggc accggccgga    5640
tctcacttac ccgacctatt cgctctcgt ccggaccccc ggagagaaag cgccgaagca     5700
gcagcaagga gaccgccgcg atgcctgtag cgctgtgcgc gatgtcgcac tcccccctga    5760
tgggacgcaa cgaccccgaa caggaagtca tcgacgccgt cgacgccgca ttcgaccacg    5820
cgcgccggtt cgtcgccgac ttcgcccccg atctcatcgt catcttcgcc cccgaccact    5880
acaacggcgt cttctacgac ctgctgccgc cgttctgtat cggtgccgcc gcgcagtccg    5940
tcggcgacta cggcaccgaa gccggccctc tcgacgtcga ccgtgacgcc gcctacgcag    6000
tcgcccgcga cgtcctcgac agcggcatcg acgtcgcatt ctccgaacgc atgcacgtcg    6060
accacggatt cgcccaagca ctccaattgc tggtcggatc gatcaccgcc gtgccgaccg    6120
tgccgatctt catcaattcg gtcgccgaac cgctcggccc ggtcagccgg gtacggctgc    6180
tcggcgaggc ggtcgggcgg gccgctgcca agctggacaa gcgtgtgctg ttcgtcggat    6240
ccggcggcct gtcccacgac ccgccggtcc cgcagttcgc caccgcgcca gaggaagtgc    6300
gcgagcggtt gatcgacggc cgcaatccca gtgccgccga acgtgatgcc cgcgaacagc    6360
gcgtcatcac cgccgggcgg gacttcgccg ccggcaccgc cgccatccag ccactgaacc    6420
ccgaatggga ccggcacctg ctcgacgtcc tcgcctccgg cgacctcgag cagatcgacg    6480
cgtggaccaa cgactggttc gtcgaacagg ccggacactc ctcccacgaa gtgcgcacct    6540
ggatcgccgc gtacgcggca atgagcgccc cgggaagta ccgcgtcacc tcgaccttct     6600
accgcgaaat ccacgagtgg atagcaggat tcgggattac taccgccgtc gccgtcgacg    6660
aatagacccc gccgctcccg cccccgcagtc ccaacgaagg gtggccccgg atgacctccg    6720
tccgcccgtg ctcgccgtcg gtgaacgcgg gctggtcggt gggcaggaag acctcatcgc    6780
cgacatcgcc ctcgacctcg cagctcgtca gtaggaatgc gcacgggccg acgagtcgcg    6840
ctggtcaccg gggccagccg cggcatcggg gcggccatcg cagatgcggt ggccgcctcc    6900
ggtgccgcca taatcgtcca ctacggatcc gatcggacgg ccgccgctgc ggtgtcgacg    6960
gcatcacggc tgccgggggc ctcgcggctg cggtccaggc cgacctgtcc cgacccgagg    7020
ggcctgaaga gctgatgcgg gagttcgact ccgcgctcga cggtctcggg ctcgaccgag    7080
ggctcgacat cctcgtcaac aacgccggaa tcagtcggcg cggagcgctc gagcgcgtca    7140
ctgtcgagga tttcgaccgt ctggtcgcac tcaaccagcg cgcccgttc ttcgtgactc      7200 ggcatgccct gccccggatg cacgacggcg gtcgcatcgt caacatttcc tccggatccg    7260
cccgctacgc cagacccgac gtcatcagct acgccatgac caaggggcg atcgaggtgc     7320 tcacccgcgc cctcgccgta gacgtcggcg aacgaggcat caccgccaac gccgtggcgc    7380
```

| | |
|---|---:|
| cggccgcgct cgataccgac atgaacgcgc actggcttcg cggtgacgac catgcccgca | 7440 |
| ccaccgccgc gtccaccact gcactgcgaa aactcgccac cgcggaggac atcgccgcga | 7500 |
| tcgtggcctt cctcgtcagc gccgccgccg gtgcgatcac cgggcaggtc atcgacgcca | 7560 |
| ccaacggcaa ccggctctaa ccag | 7584 |

<210> SEQ ID NO 2
<211> LENGTH: 7584
<212> TYPE: DNA
<213> ORGANISM: Rhodococcus corallina

<400> SEQUENCE: 2

| | |
|---|---:|
| ctggttagag ccggttgccg ttggtggcgt cgatgacctg cccggtgatc gcaccggcgg | 60 |
| cggcgctgac gaggaaggcc acgatcgcgg cgatgtcctc cgcggtggcg agttttcgca | 120 |
| gtgcagtggt ggacgcggcg gtggtgcggg catggtcgtc accgcgaagc cagtgcgcgt | 180 |
| tcatgtcggt atcgagcgcg gccggcgcca ggcgttggc ggtgatgcct cgttcgccga | 240 |
| cgtctacggc gagggcgcgg gtgagcacct cgatcgcccc cttggtcatg gcgtagctga | 300 |
| tgacgtcggg tctggcgtag cgggcggatc cggaggaaat gttgacgatg cgaccgccgt | 360 |
| cgtgcatccg gggcagggca tgccgagtca cgaagaacgg ggcgcgctgg ttgagtgcga | 420 |
| ccagacggtc gaaatcctcg acagtgacgc gctcgagcgc tccgcgccga ctgattccgg | 480 |
| cgttgttgac gaggatgtcg agccctcggt cgagcccgag accgtcgagc gcggagtcga | 540 |
| actcccgcat cagctcttca ggcccctcgg gtcgggacag gtcggcctgg accgcagccg | 600 |
| cgaggccccc ggcagccgtg atgccgtcga caccgcagcg gcggccgtcc gatcggatcc | 660 |
| gtagtggacg attacggcgg caccggaggc ggccaccgca tctgcgatgg ccgccccgat | 720 |
| gccgcggctg gccccggtga ccagcgcgac tcgtcggccc gtgcgcattc ctactgacga | 780 |
| gctgcgaggt cgagggcgat gtcggcgatg aggtcttcct gcccaccgac cagcccgcgt | 840 |
| tcaccgacgg cgagcacggg cggacggagg tcatccgggg ccaccgttcg ttgggactgc | 900 |
| ggggcgggag cggcggggtc tattcgtcga cggcgacggc ggtagtaatc ccgaatcctg | 960 |
| ctatccactc gtggatttcg cggtagaagg tcgaggtgac gcggtacttc ccggcggcgc | 1020 |
| tcattgccgc gtacgcggcg atccaggtgc gcacttcgtg ggaggagtgt ccggcctgtt | 1080 |
| cgacgaacca gtcgttggtc cacgcgtcga tctgctcgag gtcgccggag gcgaggacgt | 1140 |
| cgagcaggtg ccggtcccat cgggggttca gtggctggat ggcggcgtg ccggcggcga | 1200 |
| agtcccgccc ggcggtgatg acgcgctgtt cgcgggcatc acgttcggcg gcactgggat | 1260 |
| tgcggccgtc gatcaaccgc tcgcgcactt cctctggcgc ggtggcgaac tgcgggaccg | 1320 |
| gcgggtcgtg gacaggccg ccggatccga cgaacacac acgcttgtcc agcttggcag | 1380 |
| cggcccgccc gaccgcctcg ccgagcagcc gtacccggct gaccgggccg agcggttcgg | 1440 |
| cgaccgaatt gatgaagatc ggcacggtcg gcacggcggt gatcgatccg accagcaatt | 1500 |
| ggagtgcttg ggcgaatccg tggtcgacgt gcatgcgttc ggagaatgcg acgtcgatgc | 1560 |
| cgctgtcgag gacgtcgcgg gcgactgcgt aggcggcgtc acgtcgacg tcgagagggc | 1620 |
| cggcttcggt gccgtagtcg ccgacggact gcgcggcggc accgatacag aacggcggca | 1680 |
| gcaggtcgta gaagacgccg ttgtagtggt cgggggcgaa gatgacgatg agatcggggg | 1740 |
| cgaagtcggc gacgaaccgg cgcgcgtggt cgaatgcggc gtcgacggcg tcgatgactt | 1800 |
| cctgttcggg gtcgttgcgt cccatcaggg gggagtgcga catcgcgcac agcgctacag | 1860 |
| gcatcgcggc ggtctccttg ctgctgcttc ggcgctttct ctccgggggt ccggacgaga | 1920 |

```
gcgcaatagg tcgggtaagt gagatccggc cggtgccgcc cgggttgcag gggttggcgg    1980
caccggccgg ggtctgtgtc agctgcgacc gaggaggaag tccagatgca gcttgttgaa    2040
ggtctcgggg tcctcgtact ggggccagtg gccacagttc tccatgatgg ccagcttggc    2100
gcccgggatg tgggaggcga tgcgcttggc ttcgtcgacc ggaccggagg ggtccttggt    2160
ggtccacagc accatcgcgg gcaccgtgat gccgttgaga gtggcgtcgg tgatcatgtt    2220
ccgcttgcgg gtttcgaggt cctgcagtgc catgttcatc tcgcaggcct tgagccaatc    2280
cggctgctgg aagatggcct ggcgggtgcg gatcaggtcg tcggtgacca tggtcgggtc    2340
ggccatgagc cattcgaggc gtgctttgac gcgttcccag ctcgggtcct tcgccgcttc    2400
catcgacagg gtatagagac gttccatcac ctgagggttg gccatggtgc cgcccatggt    2460
gttgagcacg atccggtcga ccttctcggg atggtcgtgc gcgaactggg cggtgaccca    2520
accgccgaga gactccccgg aaaacgaggc cttctcgacg ccgatggcgt ccagcaactg    2580
cagcacgtgg tcgatgtagt gcttgatctc gagcgggtgg tcgggcttgg tcgaatagcc    2640
gtggccgatg aagtcgattg cccagacgtt gaagtgctcg gaatgcgagc gcagattgcg    2700
cacgtacgcc tcggcgtggc cggtgatgcc gtgcagcagg atcagcgtgg gcttggacga    2760
atcgccggcg tgcaggtatc gggtccggta ggggccggcc tggatgaatc cctggctgaa    2820
ctcgacctgg ttcaggtcgt cccagacgct ggtgtaagga cgggtcatcg gttctctccc    2880
tcgactgtgg tggtgcgggt ggcggaagct ggtgctgcat cctcggcggt aacgtgcgga    2940
acgacgatcg gcacggcccg ggtgctgtac tgcggctcgt tgtgccgct cgggttcccg     3000 ttgtcgctgg ccgagtggtc gaggaccgcg gtgagagcgt tctcgaggct ggtgagcgct    3060
tcggtgtcgt cccagaccgg agcactgtgt cgccacgcga cgtagccgtc gggccgcacg    3120
agcagggcgc cggcctcgtc gatgtcgcgg acccgccgcc agtatccgta agggtcgatg    3180
gtgccgggtt cgccgacaac gacggtccgc aggaacggca ggtcgagttt ggcggcggca    3240
cgcttccatg cctggccgcc gagtccggtc agcagggtca tcattccctt gccggtgacg    3300
tcgagggtgg agatgcgggt tccgtcggcg ccgaccagcc acgcatgcgg cagcttcgcg    3360
cccggccggg tggtggcctg caggtacagc tcacgatcgc gcacccacac ttcctcgccc    3420
gcctcggggt cgggaacgac cgcggacgag gtgtagcgct ggttgagttc gacgccctgg    3480
gcgttgaatt cggcgttctt cacctccagc gcctcgtaca gccgctcacg cagagcaaca    3540
ccttcggacg agggttcctt caactttgcc aggccggcgg cgaccgggtc gtcgctctcg    3600
tgatcgaacc attcgcgcag cccggcgtag tccttgcggg actggttggc gcgagcgacg    3660
atctgtttgc cgaccggaac acgctcagga gagtaggact cgagcagacc cggtcctgca    3720
taccccttca cgacgaacgc gatcttccat gccaggttga acgcgtcctg catggacgtg    3780
ttcgagccca gcccgctgct cggcggatgc cggtgcaccg cgtcgccgcc gcagaacact    3840
cgaccggact ggtagtgctc agcccactgc cggttgacgt accagaagga cctcgacacg    3900
atctcgacgt ccaggtgcgg gtcgccgacg agggtccgga tctgttcgag gacaacgtcg    3960
tcggagacat ccggctcgcc gttcgccatg tcgaagcccc agccggcgat ccactggtcc    4020
cacggtcgga tcgcgcgcag cagacccatg ccgatctcac cgaaaccggc cttcgagttg    4080
acgatccagt gcaagatgct cggccgatga gcgacatatt tgctcaggtc cgcgttgaac    4140
aggatgtacg cggtaccggc gcgggcgagt tcaccttcga acggaagccc gatctgttcg    4200
gcgatcttcg atcgtgcgcc gtcgaaaccg agcaggaagc gggctcgctg ggtgaacacg    4260
```

-continued

```
gtgcccgagc ggacgtcgcg gaaccggacg gtcaccccgt cctcgtcctg ggcgtggtcg    4320
aggtattcgg tgttgaagct gatgaccgca ccacgttcgg cggcgttctt gatcagcacc    4380
ggctccatca ggggctgcgg aatgtcgagc atcgtgcagg ggcttccgga caggtagtcc    4440
ccgtagcgga tatcgcccgt accccaggtc tgcatccgga cgatctcctc gccggccagg    4500
ctcgtggtga acagcgtgtc gcccatctgg tcccacgggg tggcgtagtt gcgcgcctcg    4560
tcttcgacgc ccaggtcacg cagcacttcg acggcgcgct ggttggtgat gtgcgcgcgc    4620
ggcgagttcg ccacccaggg gaacatcgag acggcgtgaa cgcggatgcc gtagctggcc    4680
agggcaagcg ccgctgtgcc accggcgggg ccgaggccga cgatcacgac gtcggtgtcg    4740
taggaggtgc ggtcgtggtc actcatgtct gtcatcactt cacttgtcga ggacgcgcag    4800
ggatgctgcg gtgtccggaa ctgtccgagt cgaaaatgtt tcggtgtcag gcattttcgg    4860
tgtggaggtg gcctggtcgc gagtgagctg gctcgcagcg cccttgcgcc cccagccgcc    4920
gggcagcagg atcaccgaga cgatcgagat ggccgagacg atcagcaggt aggtcacgat    4980
cgagttgctg gtgttggtgg aggcgtacaa ggcggtcgcg atcgtcgggg cgaacgcgga    5040
gccggcgacc tgggagatgg tgtagccgat agagacaccg ctgtagcgca cgtccgcgtc    5100
gaagaccatc gtgaacaggg agcctgtcac gccggcggcg ggggccattg caattccgaa    5160
gaccagcacc tgcgcggcca tgaacagcca cgggttgccg tgttgatca gtgcgaaggc    5220 gggggcgatc accacaccca tcgcggcggc gccgagcagg tacatggtct tgcggccgaa    5280
agtgtcggac agagcgccga acacgaggta gaggaggacg cgacgatgc cggcgacgaa    5340 tactccggcc agggcgaagg tgcggctgat ccccgcgacg gtggtgccgt aggagacgag    5400
gtaggccatg cagatatagg cgaacactcc ttgggacagg taggtgcccg cgatgaggag    5460
aatttccttc cagtgcttgc ggaacgcttc ggcgatcggc attcgcacca cggcgctctg    5520
tgccttcacc tcggcgaagt cggggctttc ggccagggac aggcgaatga acagcccgat    5580
cacgatcagc accgcgctga acaggaacgg cagtcgccag ccccaactca ggaactgctc    5640
gtcgggcaat tgggagaccg cgaagaacgc cagggttgcg acgctggtcc cggcgggtgc    5700
ccccatctgg gagaaggatc cgaaaaagcc cttcttcgcg gtgggggcgt gctcgacggc    5760
catcagggtg gctccacccc actcgccgcc gacggcaaag ccctgcacca ggcgcagcag    5820
ggtcagcagg atggggcgg cgatcccgat ttgggcgtaa ccgggcaaca atcccatcag    5880
tacggtggcc gagcccattc cgaccaggga gatcaccagc atctgcttgc ggccgacccg    5940
gtcaccgaag tgcccgaaca ctatgccacc cagcgggcgg cgaggaacc caacgctgaa    6000 ggtcgcgaac gacaacagga ttccgatcgc ggacgagaca tccggaaga acaactcagg    6060 gaataccagc gcggccgcgg tgccgtagat gaagaagtcg tagtactcga cggtggtacc    6120
gatgaagctg gccatcgcta cccgcagcgg tgaggtcttc gtcggggagg taggtgtggt    6180
gctcacggtc gggcttcccc gatctgtggg cggaagtggg ctcgtgcccc gaaggacgat    6240
gcgtgcgaag cggtcgtcat ggccgctcct ttcttctggg gatgttcgag aggggttctc    6300
tggagaatct tcgagaggga gcactcaact agaatgctag acgtctagtt cagacgctac    6360
tcgggcatag agggtgacgc aagtctctgg atgagggtaa aggtgatcga cggcgcgccg    6420
gccctctagg gcgagacagg ggtcagcgtg gagggtgccg gtggatcgtc tgcagcgcta    6480
cggccgagag tccccctcg gcgtaggtgg cgcgatagcg gagccggtcg atgggcccggg    6540 tatcggggtc tagctcggca gctgggcgtt ggattcgtcg cggattactg cgatggtgcc    6600
gacgatgtgg cgttccatgg cctcgcgggc ggcagctgcg tcacggttgc ggatggcctc    6660
```

```
ggtgatttcg tggtggtcat gctgccggtc gggcagtgcg ctcgagagcg ggttggtgat    6720
gccggtggtg ttgatcaaga agtccgacag atcccacatt cgctggctgg tctcctccat    6780
gatccgcgag tgcgccatcg cgtggatggc cgcatggaac tcccggttgt gcacgcggta    6840
cccgcgggcg cggaccaccg ggtcgtggga ggtgatcagg gcgtcgaccc gcgccgagat    6900
caggtccagc tccagcaact gggcctcggt ccgccgggag gccgctaccg cggcgatggt    6960
cccttcgaaa ccgccgaaca gggtgtagaa gtcttccact tcgcgcgggg cgtaggagac    7020
gacctcgcaa ccgacctggg gaacgatgtg gaccagcttg tcgctggaca ggcggcgcag    7080
agcgtccatg acgggctgct tgctcacccc gaactcttgc cggatcgact cgacgacgat    7140
cttctcgcct gccgcatagc gcccttcgag cagccggttc ttcagaatgt cgtacaacgc    7200
ggaggacagc cgcgcccccg aggtgcggac attggcgagc agggcggcgg cctcactgcc    7260
cggcttgggg ccggtgtcgg tggtggtcat cgagtcaggc tttccgtcgg cgtcccggac    7320
atggctcccc cttatgccgc ggcgctcacc gcaacagctt gcattctagt acttgtggtg    7380
tgagtcactg tgggttacct tcgtctggaa cgctagcatt ccagacctga tggccggggc    7440
atcgtggcca acctcggggt taacgccgga gggcacgccg tacgcgccat atccaggcac    7500
ccggacatgc gccctctgcg ggcgacaggc cgagcagtgc cctcggcaac gcgggccaca    7560
tgcaaggaga agaacatgga attc                                           7584
```

<210> SEQ ID NO 3
<211> LENGTH: 246
<212> TYPE: PRT
<213> ORGANISM: Rhodococcus corallina

<400> SEQUENCE: 3

```
Met Thr Thr Thr Asp Thr Gly Pro Lys Pro Gly Ser Glu Ala Ala Ala
 1               5                  10                  15

Leu Leu Ala Asn Val Arg Thr Ser Gly Ala Arg Leu Ser Ser Ala Leu
            20                  25                  30

Tyr Asp Ile Leu Lys Asn Arg Leu Leu Glu Gly Arg Tyr Ala Ala Gly
        35                  40                  45

Glu Lys Ile Val Val Glu Ser Ile Arg Gln Glu Phe Gly Val Ser Lys
    50                  55                  60

Gln Pro Val Met Asp Ala Leu Arg Arg Leu Ser Ser Asp Lys Leu Val
65                  70                  75                  80

His Ile Val Pro Gln Val Gly Cys Glu Val Val Ser Tyr Ala Pro Arg
                85                  90                  95

Glu Val Glu Asp Phe Tyr Thr Leu Phe Gly Gly Phe Glu Gly Thr Ile
            100                 105                 110

Ala Ala Val Ala Ala Ser Arg Arg Thr Glu Ala Gln Leu Leu Glu Leu
        115                 120                 125

Asp Leu Ile Ser Ala Arg Val Asp Ala Leu Ile Thr Ser His Asp Pro
    130                 135                 140

Val Val Arg Ala Arg Gly Tyr Arg Val His Asn Arg Glu Phe His Ala
145                 150                 155                 160

Ala Ile His Ala Met Ala His Ser Arg Ile Met Glu Glu Thr Ser Gln
                165                 170                 175

Arg Met Trp Asp Leu Ser Asp Phe Leu Ile Asn Thr Thr Gly Ile Thr
            180                 185                 190

Asn Pro Leu Ser Ser Ala Leu Pro Asp Arg Gln His Asp His His Glu
        195                 200                 205
```

-continued

```
Ile Thr Glu Ala Ile Arg Asn Arg Asp Ala Ala Ala Arg Glu Ala
    210                 215                 220

Met Glu Arg His Ile Val Gly Thr Ile Ala Val Ile Arg Asp Glu Ser
225                 230                 235                 240

Asn Ala Gln Leu Pro Ser
                245

<210> SEQ ID NO 4
<211> LENGTH: 451
<212> TYPE: PRT
<213> ORGANISM: Rhodococcus corallina

<400> SEQUENCE: 4

Met Ala Ser Phe Ile Gly Thr Thr Val Glu Tyr Tyr Asp Phe Phe Ile
1               5                   10                  15

Tyr Gly Thr Ala Ala Ala Leu Val Phe Pro Glu Leu Phe Phe Pro Asp
                20                  25                  30

Val Ser Ser Ala Ile Gly Ile Leu Leu Ser Phe Ala Thr Phe Ser Val
            35                  40                  45

Gly Phe Leu Ala Arg Pro Leu Gly Gly Ile Val Phe Gly His Phe Gly
        50                  55                  60

Asp Arg Val Gly Arg Lys Gln Met Leu Val Ile Ser Leu Val Gly Met
65                  70                  75                  80

Gly Ser Ala Thr Val Leu Met Gly Leu Leu Pro Gly Tyr Ala Gln Ile
                85                  90                  95

Gly Ile Ala Ala Pro Ile Leu Leu Thr Leu Leu Arg Leu Val Gln Gly
                100                 105                 110

Phe Ala Val Gly Gly Glu Trp Gly Gly Ala Thr Leu Met Ala Val Glu
            115                 120                 125

His Ala Pro Thr Ala Lys Lys Gly Phe Phe Gly Ser Phe Ser Gln Met
        130                 135                 140

Gly Ala Pro Ala Gly Thr Ser Val Ala Thr Leu Ala Phe Phe Ala Val
145                 150                 155                 160

Ser Gln Leu Pro Asp Glu Gln Phe Leu Ser Trp Gly Trp Arg Leu Pro
                165                 170                 175

Phe Leu Phe Ser Ala Val Leu Ile Val Ile Gly Leu Phe Ile Arg Leu
                180                 185                 190

Ser Leu Ala Glu Ser Pro Asp Phe Ala Glu Val Lys Ala Gln Ser Ala
            195                 200                 205

Val Val Arg Met Pro Ile Ala Glu Ala Phe Arg Lys His Trp Lys Glu
        210                 215                 220

Ile Leu Leu Ile Ala Gly Thr Tyr Leu Ser Gln Gly Val Phe Ala Tyr
225                 230                 235                 240

Ile Cys Met Ala Tyr Leu Val Ser Tyr Gly Thr Thr Val Ala Gly Ile
                245                 250                 255

Ser Arg Thr Phe Ala Leu Ala Gly Val Phe Ala Gly Ile Val Ala
            260                 265                 270

Val Leu Leu Tyr Leu Val Phe Gly Ala Leu Ser Asp Thr Phe Gly Arg
        275                 280                 285

Lys Thr Met Tyr Leu Leu Gly Ala Ala Met Gly Val Val Ile Ala
            290                 295                 300

Pro Ala Phe Ala Leu Ile Asn Thr Gly Asn Pro Trp Leu Phe Met Ala
305                 310                 315                 320

Ala Gln Val Leu Val Phe Gly Ile Ala Met Ala Pro Ala Ala Gly Val
```

```
                        325                 330                 335
Thr Gly Ser Leu Phe Thr Met Val Phe Asp Ala Asp Val Arg Tyr Ser
            340                 345                 350

Gly Val Ser Ile Gly Tyr Thr Ile Ser Gln Val Ala Gly Ser Ala Phe
            355                 360                 365

Ala Pro Thr Ile Ala Thr Ala Leu Tyr Ala Ser Thr Asn Thr Ser Asn
            370                 375                 380

Ser Ile Val Thr Tyr Leu Leu Ile Val Ser Ala Ile Ser Ile Val Ser
385                 390                 395                 400

Val Ile Leu Leu Pro Gly Gly Trp Gly Arg Lys Gly Ala Ala Ser Gln
                405                 410                 415

Leu Thr Arg Asp Gln Ala Thr Ser Thr Pro Lys Met Pro Asp Thr Glu
            420                 425                 430

Thr Phe Ser Thr Arg Thr Val Pro Asp Thr Ala Ala Ser Leu Arg Val
            435                 440                 445

Leu Asp Lys
    450

<210> SEQ ID NO 5
<211> LENGTH: 636
<212> TYPE: PRT
<213> ORGANISM: Rhodococcus corallina

<400> SEQUENCE: 5

Met Thr Asp Met Ser Asp His Asp Arg Thr Ser Tyr Asp Thr Asp Val
1               5                   10                  15

Val Ile Val Gly Leu Gly Pro Ala Gly Gly Thr Ala Ala Leu Ala Leu
                20                  25                  30

Ala Ser Tyr Gly Ile Arg Val His Ala Val Ser Met Phe Pro Trp Val
            35                  40                  45

Ala Asn Ser Pro Arg Ala His Ile Thr Asn Gln Arg Ala Val Glu Val
        50                  55                  60

Leu Arg Asp Leu Gly Val Glu Asp Glu Ala Arg Asn Tyr Ala Thr Pro
65                  70                  75                  80

Trp Asp Gln Met Gly Asp Thr Leu Phe Thr Thr Ser Leu Ala Gly Glu
                85                  90                  95

Glu Ile Val Arg Met Gln Thr Trp Gly Thr Gly Asp Ile Arg Tyr Gly
            100                 105                 110

Asp Tyr Leu Ser Gly Ser Pro Cys Thr Met Leu Asp Ile Pro Gln Pro
        115                 120                 125

Leu Met Glu Pro Val Leu Ile Lys Asn Ala Ala Glu Arg Gly Ala Val
130                 135                 140

Ile Ser Phe Asn Thr Glu Tyr Leu Asp His Ala Gln Asp Glu Asp Gly
145                 150                 155                 160

Val Thr Val Arg Phe Arg Asp Val Arg Ser Gly Thr Val Phe Thr Gln
                165                 170                 175

Arg Ala Arg Phe Leu Leu Gly Phe Asp Gly Ala Arg Ser Lys Ile Ala
            180                 185                 190

Glu Gln Ile Gly Leu Pro Phe Glu Gly Glu Leu Ala Arg Ala Gly Thr
        195                 200                 205

Ala Tyr Ile Leu Phe Asn Ala Asp Leu Ser Lys Tyr Val Ala His Arg
    210                 215                 220

Pro Ser Ile Leu His Trp Ile Val Asn Ser Lys Ala Gly Phe Gly Glu
225                 230                 235                 240
```

```
Ile Gly Met Gly Leu Leu Arg Ala Ile Arg Pro Trp Asp Gln Trp Ile
            245                 250                 255

Ala Gly Trp Gly Phe Asp Met Ala Asn Gly Glu Pro Asp Val Ser Asp
            260                 265                 270

Asp Val Leu Glu Gln Ile Arg Thr Leu Val Gly Asp Pro His Leu
            275                 280                 285

Asp Val Glu Ile Val Ser Arg Ser Phe Trp Tyr Val Asn Arg Gln Trp
        290                 295                 300

Ala Glu His Tyr Gln Ser Gly Arg Val Phe Cys Gly Asp Ala Val
305                 310                 315                 320

His Arg His Pro Pro Ser Ser Gly Leu Gly Ser Asn Thr Ser Met Gln
                325                 330                 335

Asp Ala Phe Asn Leu Ala Trp Lys Ile Ala Phe Val Val Lys Gly Tyr
            340                 345                 350

Ala Gly Pro Gly Leu Leu Glu Ser Tyr Ser Pro Glu Arg Val Pro Val
            355                 360                 365

Gly Lys Gln Ile Val Ala Arg Ala Asn Gln Ser Arg Lys Asp Tyr Ala
        370                 375                 380

Gly Leu Arg Glu Trp Phe Asp His Glu Ser Asp Pro Val Ala Ala
385                 390                 395                 400

Gly Leu Ala Lys Leu Lys Glu Pro Ser Ser Glu Gly Val Ala Leu Arg
                405                 410                 415

Glu Arg Leu Tyr Glu Ala Leu Glu Val Lys Asn Ala Glu Phe Asn Ala
            420                 425                 430

Gln Gly Val Glu Leu Asn Gln Arg Tyr Thr Ser Ser Ala Val Val Pro
        435                 440                 445

Asp Pro Glu Ala Gly Glu Val Trp Val Arg Asp Arg Glu Leu Tyr
450                 455                 460

Leu Gln Ala Thr Thr Arg Pro Gly Ala Lys Leu Pro His Ala Trp Leu
465                 470                 475                 480

Val Gly Ala Asp Gly Thr Arg Ile Ser Thr Leu Asp Val Thr Gly Lys
                485                 490                 495

Gly Met Met Thr Leu Leu Thr Gly Leu Gly Gln Ala Trp Lys Arg
            500                 505                 510

Ala Ala Ala Lys Leu Asp Leu Pro Phe Leu Arg Thr Val Val Gly
        515                 520                 525

Glu Pro Gly Thr Ile Asp Pro Tyr Gly Tyr Trp Arg Arg Val Arg Asp
530                 535                 540

Ile Asp Glu Ala Gly Ala Leu Leu Val Arg Pro Asp Gly Tyr Val Ala
545                 550                 555                 560

Trp Arg His Ser Ala Pro Val Trp Asp Thr Glu Ala Leu Thr Ser
            565                 570                 575

Leu Glu Asn Ala Leu Thr Ala Val Leu Asp His Ser Ala Ser Asp Asn
            580                 585                 590

Gly Asn Pro Ser Gly Thr Asn Glu Pro Gln Tyr Ser Thr Arg Ala Val
        595                 600                 605

Pro Ile Val Val Pro His Val Thr Ala Glu Asp Ala Pro Ala Ser
610                 615                 620

Ala Thr Arg Thr Thr Thr Val Glu Gly Glu Asn Arg
625                 630                 635

<210> SEQ ID NO 6
<211> LENGTH: 289
<212> TYPE: PRT
```

<213> ORGANISM: Rhodococcus corallina

<400> SEQUENCE: 6

```
Met Thr Arg Pro Tyr Thr Ser Val Trp Asp Asp Leu Asn Gln Val Glu
 1               5                  10                  15

Phe Ser Gln Gly Phe Ile Gln Ala Gly Pro Tyr Arg Thr Arg Tyr Leu
             20                  25                  30

His Ala Gly Asp Ser Ser Lys Pro Thr Leu Ile Leu Leu His Gly Ile
         35                  40                  45

Thr Gly His Ala Glu Ala Tyr Val Arg Asn Leu Arg Ser His Ser Glu
     50                  55                  60

His Phe Asn Val Trp Ala Ile Asp Phe Ile Gly His Gly Tyr Ser Thr
 65                  70                  75                  80

Lys Pro Asp His Pro Leu Glu Ile Lys Tyr Ile Asp His Val Leu
                 85                  90                  95

Gln Leu Leu Asp Ala Ile Gly Val Glu Lys Ala Ser Phe Ser Gly Glu
             100                 105                 110

Ser Leu Gly Gly Trp Val Thr Ala Gln Phe Ala His Asp His Pro Glu
         115                 120                 125

Lys Val Asp Arg Ile Val Leu Asn Thr Met Gly Gly Thr Met Ala Asn
     130                 135                 140

Pro Gln Val Met Glu Arg Leu Tyr Thr Leu Ser Met Glu Ala Ala Lys
145                 150                 155                 160

Asp Pro Ser Trp Glu Arg Val Lys Ala Arg Leu Glu Trp Leu Met Ala
                165                 170                 175

Asp Pro Thr Met Val Thr Asp Asp Leu Ile Arg Thr Arg Gln Ala Ile
            180                 185                 190

Phe Gln Gln Pro Asp Trp Leu Lys Ala Cys Glu Met Asn Met Ala Leu
        195                 200                 205

Gln Asp Leu Glu Thr Arg Lys Arg Asn Met Ile Thr Asp Ala Thr Leu
    210                 215                 220

Asn Gly Ile Thr Val Pro Ala Met Val Leu Trp Thr Thr Lys Asp Pro
225                 230                 235                 240

Ser Gly Pro Val Asp Glu Ala Lys Arg Ile Ala Ser His Ile Pro Gly
                245                 250                 255

Ala Lys Leu Ala Ile Met Glu Asn Cys Gly His Trp Pro Gln Tyr Glu
            260                 265                 270

Asp Pro Glu Thr Phe Asn Lys Leu His Leu Asp Phe Leu Leu Gly Arg
        275                 280                 285

Ser
```

<210> SEQ ID NO 7
<211> LENGTH: 314
<212> TYPE: PRT
<213> ORGANISM: Rhodococcus corallina

<400> SEQUENCE: 7

```
Met Pro Val Ala Leu Cys Ala Met Ser His Ser Pro Leu Met Gly Arg
 1               5                  10                  15

Asn Asp Pro Glu Gln Glu Val Ile Asp Ala Val Asp Ala Ala Phe Asp
             20                  25                  30

His Ala Arg Arg Phe Val Ala Asp Phe Ala Pro Asp Leu Ile Val Ile
         35                  40                  45

Phe Ala Pro Asp His Tyr Asn Gly Val Phe Tyr Asp Leu Leu Pro Pro
     50                  55                  60
```

```
Phe Cys Ile Gly Ala Ala Ala Gln Ser Val Gly Asp Tyr Gly Thr Glu
 65                  70                  75                  80

Ala Gly Pro Leu Asp Val Asp Arg Asp Ala Tyr Ala Val Ala Arg
                 85                  90                  95

Asp Val Leu Asp Ser Gly Ile Asp Val Ala Phe Ser Glu Arg Met His
                100                 105                 110

Val Asp His Gly Phe Ala Gln Ala Leu Gln Leu Val Gly Ser Ile
            115                 120                 125

Thr Ala Val Pro Thr Val Pro Ile Phe Ile Asn Ser Val Ala Glu Pro
130                 135                 140

Leu Gly Pro Val Ser Arg Val Arg Leu Leu Gly Glu Ala Val Gly Arg
145                 150                 155                 160

Ala Ala Ala Lys Leu Asp Lys Arg Val Leu Phe Val Gly Ser Gly Gly
                165                 170                 175

Leu Ser His Asp Pro Pro Val Pro Gln Phe Ala Thr Ala Pro Glu Glu
                180                 185                 190

Val Arg Glu Arg Leu Ile Asp Gly Arg Asn Pro Ser Ala Ala Glu Arg
                195                 200                 205

Asp Ala Arg Glu Gln Arg Val Ile Thr Ala Gly Arg Asp Phe Ala Ala
210                 215                 220

Gly Thr Ala Ala Ile Gln Pro Leu Asn Pro Glu Trp Asp Arg His Leu
225                 230                 235                 240

Leu Asp Val Leu Ala Ser Gly Asp Leu Glu Gln Ile Asp Ala Trp Thr
                245                 250                 255

Asn Asp Trp Phe Val Glu Gln Ala Gly His Ser Ser His Glu Val Arg
                260                 265                 270

Thr Trp Ile Ala Ala Tyr Ala Ala Met Ser Ala Ala Gly Lys Tyr Arg
                275                 280                 285

Val Thr Ser Thr Phe Tyr Arg Glu Ile His Glu Trp Ile Ala Gly Phe
                290                 295                 300

Gly Ile Thr Thr Ala Val Ala Val Asp Glu
305                 310

<210> SEQ ID NO 8
<211> LENGTH: 289
<212> TYPE: PRT
<213> ORGANISM: Rhodococcus corallina

<400> SEQUENCE: 8

Met Thr Ser Val Arg Pro Cys Ser Pro Ser Val Asn Ala Gly Trp Ser
  1               5                  10                  15

Val Gly Arg Lys Thr Ser Ser Pro Thr Ser Pro Ser Thr Ser Gln Leu
                 20                  25                  30

Val Ser Arg Asn Ala His Gly Pro Thr Ser Arg Ala Gly His Arg Gly
             35                  40                  45

Gln Pro Arg His Arg Gly Gly His Arg Arg Cys Gly Gly Arg Leu Arg
         50                  55                  60

Cys Arg Arg Asn Arg Pro Leu Arg Ile Arg Ser Asp Gly Arg Arg Cys
 65                  70                  75                  80

Gly Val Asp Gly Ile Thr Ala Ala Gly Gly Leu Ala Ala Ala Val Gln
                 85                  90                  95

Ala Asp Leu Ser Arg Pro Glu Gly Pro Glu Glu Leu Met Arg Glu Phe
                100                 105                 110
```

```
Asp Ser Ala Leu Asp Gly Leu Gly Leu Asp Arg Gly Leu Asp Ile Leu
        115                 120                 125

Val Asn Asn Ala Gly Ile Ser Arg Arg Gly Ala Leu Glu Arg Val Thr
130                 135                 140

Val Glu Asp Phe Asp Arg Leu Val Ala Leu Asn Gln Arg Ala Pro Phe
145                 150                 155                 160

Phe Val Thr Arg His Ala Leu Pro Arg Met His Asp Gly Gly Arg Ile
                165                 170                 175

Val Asn Ile Ser Ser Gly Ser Ala Arg Tyr Ala Arg Pro Asp Val Ile
            180                 185                 190

Ser Tyr Ala Met Thr Lys Gly Ala Ile Glu Val Leu Thr Arg Ala Leu
        195                 200                 205

Ala Val Asp Val Gly Glu Arg Gly Ile Thr Ala Asn Ala Val Ala Pro
        210                 215                 220

Ala Ala Leu Asp Thr Asp Met Asn Ala His Trp Leu Arg Gly Asp Asp
225                 230                 235                 240

His Ala Arg Thr Thr Ala Ala Ser Thr Thr Ala Leu Arg Lys Leu Ala
                245                 250                 255

Thr Ala Glu Asp Ile Ala Ala Ile Val Ala Phe Leu Val Ser Ala Ala
            260                 265                 270

Ala Gly Ala Ile Thr Gly Gln Val Ile Asp Ala Thr Asn Gly Asn Arg
        275                 280                 285

Leu

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 9
cgctgatttg tattgtctg                                              19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 10
gacttccatt gttcattcc                                              19

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
aaaagacgtc ggtgcgaata agggacagtg                                  30

<210> SEQ ID NO 12
<211> LENGTH: 30
<212> TYPE: DNA
<213> ORGANISM: Artificial Sequence
```

-continued

```
<220> FEATURE:
<223> OTHER INFORMATION: Description of Artificial Sequence: Primer

<400> SEQUENCE: 12
aaaagacgtc acaaaacagc agggaagcag                                        30
```